United States Patent
Hong et al.

(10) Patent No.: US 11,009,790 B2
(45) Date of Patent: May 18, 2021

(54) PHOTOACID GENERATOR AND PHOTORESIST COMPOSITION INCLUDING THE SAME

(71) Applicant: SAMSUNG ELECTRONICS CO., LTD., Suwon-si (KR)

(72) Inventors: Suk-koo Hong, Yongin-si (KR); Kyoung-yong Cho, Namyangju-si (KR); Hyo-sung Lee, Hwaseong-si (KR); Gum-hye Jeon, Hwaseong-si (KR); Mi-yeong Kang, Incheon (KR); Gun-woo Park, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 15/662,677

(22) Filed: Jul. 28, 2017

(65) Prior Publication Data
US 2018/0031967 A1 Feb. 1, 2018

(30) Foreign Application Priority Data

Jul. 28, 2016 (KR) .................. 10-2016-0096127
Jul. 27, 2017 (KR) .................. 10-2017-0095720

(51) Int. Cl.
| | | |
|---|---|---|
| G03F 7/004 | (2006.01) | |
| G03F 7/26 | (2006.01) | |
| C07C 309/05 | (2006.01) | |
| C07C 309/06 | (2006.01) | |
| C07C 309/19 | (2006.01) | |
| C07C 309/32 | (2006.01) | |
| C07C 309/39 | (2006.01) | |
| C07C 309/65 | (2006.01) | |
| C07C 309/73 | (2006.01) | |
| C07C 303/32 | (2006.01) | |
| G03F 7/027 | (2006.01) | |
| G03F 7/038 | (2006.01) | |
| G03F 7/11 | (2006.01) | |
| G03F 7/20 | (2006.01) | |
| G03F 7/039 | (2006.01) | |
| C07C 309/12 | (2006.01) | |
| C07C 309/17 | (2006.01) | |
| C07C 381/12 | (2006.01) | |
| C07D 333/46 | (2006.01) | |

(52) U.S. Cl.
CPC .......... *G03F 7/0045* (2013.01); *C07C 303/32* (2013.01); *C07C 309/05* (2013.01); *C07C 309/06* (2013.01); *C07C 309/12* (2013.01); *C07C 309/17* (2013.01); *C07C 309/65* (2013.01); *C07C 309/73* (2013.01); *C07C 381/12* (2013.01); *C07D 333/46* (2013.01); *G03F 7/0046* (2013.01); *G03F 7/027* (2013.01); *G03F 7/038* (2013.01); *G03F 7/0397* (2013.01); *G03F 7/11* (2013.01); *G03F 7/2041* (2013.01)

(58) Field of Classification Search
CPC ........ G03F 7/0392; G03F 7/30; G03F 7/0045; G03F 7/0046; C07C 309/05; C07C 309/06; C07C 309/73; C07C 309/19; C07C 309/32; C07C 309/39; C07C 309/65; C07C 303/32
USPC .............. 430/270.1, 921, 922; 562/101, 113; 568/27, 28, 34, 35
See application file for complete search history.

(56) References Cited

U.S. PATENT DOCUMENTS

| | | | |
|---|---|---|---|
| 5,569,784 A | 10/1996 | Watanabe et al. | |
| 7,101,918 B2 | 9/2006 | Ishihara et al. | |
| 7,217,492 B2 | 5/2007 | Yoneda et al. | |
| 7,531,290 B2 * | 5/2009 | Kobayashi | C07C 309/07 430/270.1 |
| 7,547,501 B2 * | 6/2009 | Dammel | C07F 5/027 430/270.1 |
| 7,678,528 B2 | 3/2010 | Rahman et al. | |

(Continued)

FOREIGN PATENT DOCUMENTS

| | | |
|---|---|---|
| JP | 2005-227680 A | 8/2005 |
| JP | 2006-259136 A | 9/2006 |
| JP | 2011-006400 A | 1/2011 |

*Primary Examiner* — John S Chu
(74) *Attorney, Agent, or Firm* — Lee IP Law, P.C.

(57) ABSTRACT

A photoacid generator (PAG) and a photoresist composition, the PAG being represented by the following Chemical Formula (I):

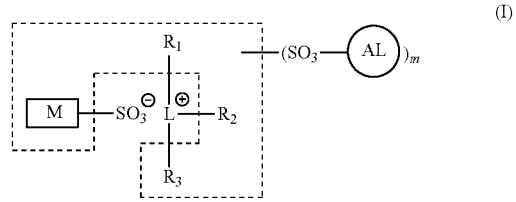

wherein, in Chemical Formula (I), L is sulfur (S) or iodine (I), $R_3$ being omitted when L is I; $R_1$, $R_2$, and $R_3$ are each independently a C1 to C10 alkyl, alkenyl, alkynyl, or alkoxy group that is unsubstituted or substituted with a heteroatom such that the heteroatom is pendant or is between the group and L, or a C6 to C18 aryl, arylalkyl, or alkylaryl group that is unsubstituted or substituted with a heteroatom such that the heteroatom is pendant or is between the group and L; AL is an acid-labile group; m is 1 to 4; and M is a C1 to C30 hydrocarbon group that is unsubstituted or substituted with a heteroatom such that the heteroatom is pendant or is between the group and a sulfur atom.

15 Claims, 12 Drawing Sheets

(56) References Cited

U.S. PATENT DOCUMENTS

| | | |
|---|---|---|
| 7,807,329 B2 | 10/2010 | Mizutani et al. |
| 8,318,403 B2 | 11/2012 | Ichikawa et al. |
| 8,652,752 B2 | 2/2014 | Hayoz et al. |
| 8,980,526 B2 | 3/2015 | Yoon et al. |
| 8,993,212 B2 | 3/2015 | Takihana et al. |
| 9,046,767 B2 | 6/2015 | Aqad et al. |
| 2010/0297541 A1 | 11/2010 | Hayoz et al. |
| 2015/0301449 A1 | 10/2015 | Ohashi et al. |

\* cited by examiner

PHOTOACID GENERATOR AND PHOTORESIST COMPOSITION INCLUDING THE SAME

CROSS-REFERENCE TO RELATED APPLICATION

Korean Patent Application No. 10-2016-0096127, filed on Jul. 28, 2016 and Korean Patent Application No. 10-2017-0095720, filed on Jul. 27, 2017, in the Korean Intellectual Property Office, and entitled: "Photoacid Generator and Photoresist Composition Including the Same," is incorporated by reference herein in its entirety.

BACKGROUND

1. Field

Embodiments relate to a photoacid generator and a photoresist composition including the same.

2. Description of the Related Art

A photoacid generator (PAG) may generate a larger amount of acids based on the same light intensity in terms of an advantage in improving productivity and realizing a pattern, and it may be advantageous to add a large amount of a photoacid generator to a photoresist composition.

SUMMARY

The embodiments may be realized by providing a photoacid generator (PAG) represented by the following Chemical Formula (I):

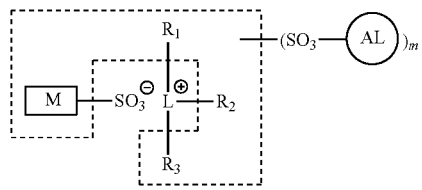

wherein, in Chemical Formula (I), L is sulfur (S) or iodine (I), $R_3$ being omitted when L is I; $R_1$, $R_2$, and $R_3$ are each independently a C1 to C10 linear, cyclic, or branched alkyl, alkenyl, alkynyl, or alkoxy group that is unsubstituted or substituted with a heteroatom such that the heteroatom is pendant or is between the group and L, or a C6 to C18 aryl, arylalkyl, or alkylaryl group that is unsubstituted or substituted with a heteroatom such that the heteroatom is pendant or is between the group and L; two of $R_1$, $R_2$, and $R_3$ being separate or being bonded to each other to form a ring in conjunction with L; AL is an acid-labile group; m is an integer of 1 to 4; and M is a C1 to C30 linear, cyclic, or branched hydrocarbon group that is unsubstituted or substituted with a heteroatom such that the heteroatom is pendant or is between the group and a sulfur atom The embodiments may be realized by providing a photoresist composition including a photosensitive resin; a photoacid generator (PAG) represented by the following Chemical Formula (I); and a solvent, the solvent being capable of dissolving the photosensitive resin and the photoacid generator represented by Chemical Formula (I),

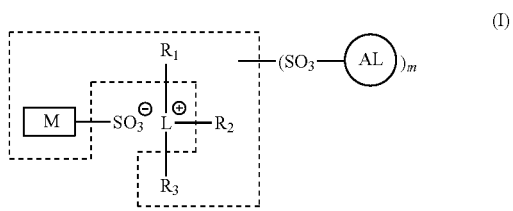

wherein, in Chemical Formula (I), L is sulfur (S) or iodine (I), $R_3$ being omitted when L is I; $R_1$, $R_2$, and $R_3$ are each independently a C1 to C10 linear, cyclic, or branched alkyl, alkenyl, alkynyl, or alkoxy group that is unsubstituted or substituted with a heteroatom such that the heteroatom is pendant or is between the group and L, or a C6 to C18 aryl, arylalkyl, or alkylaryl group that is unsubstituted or substituted with a heteroatom such that the heteroatom is pendant or is between the group and L; two of $R_1$, $R_2$, and $R_3$ being separate or being bonded to each other to form a ring in conjunction with L; AL is an acid-labile group; m is an integer of 1 to 4; and M is a C1 to C30 linear, cyclic, or branched hydrocarbon group that is unsubstituted or substituted with a heteroatom such that the heteroatom is pendant or is between the group and a sulfur atom.

The embodiments may be realized by providing a photoacid generator (PAG), the PAG including an acid labile group bonded to one sulfonate group, the acid labile group being capable of being deprotected by an acid, and another sulfonate group bonded to a sulfonium ion or an iodonium ion.

BRIEF DESCRIPTION OF THE DRAWINGS

Features will become apparent to those of ordinary skill in the art by describing in detail exemplary embodiments with reference to the attached drawings in which.

DETAILED DESCRIPTION

Figure 1A:
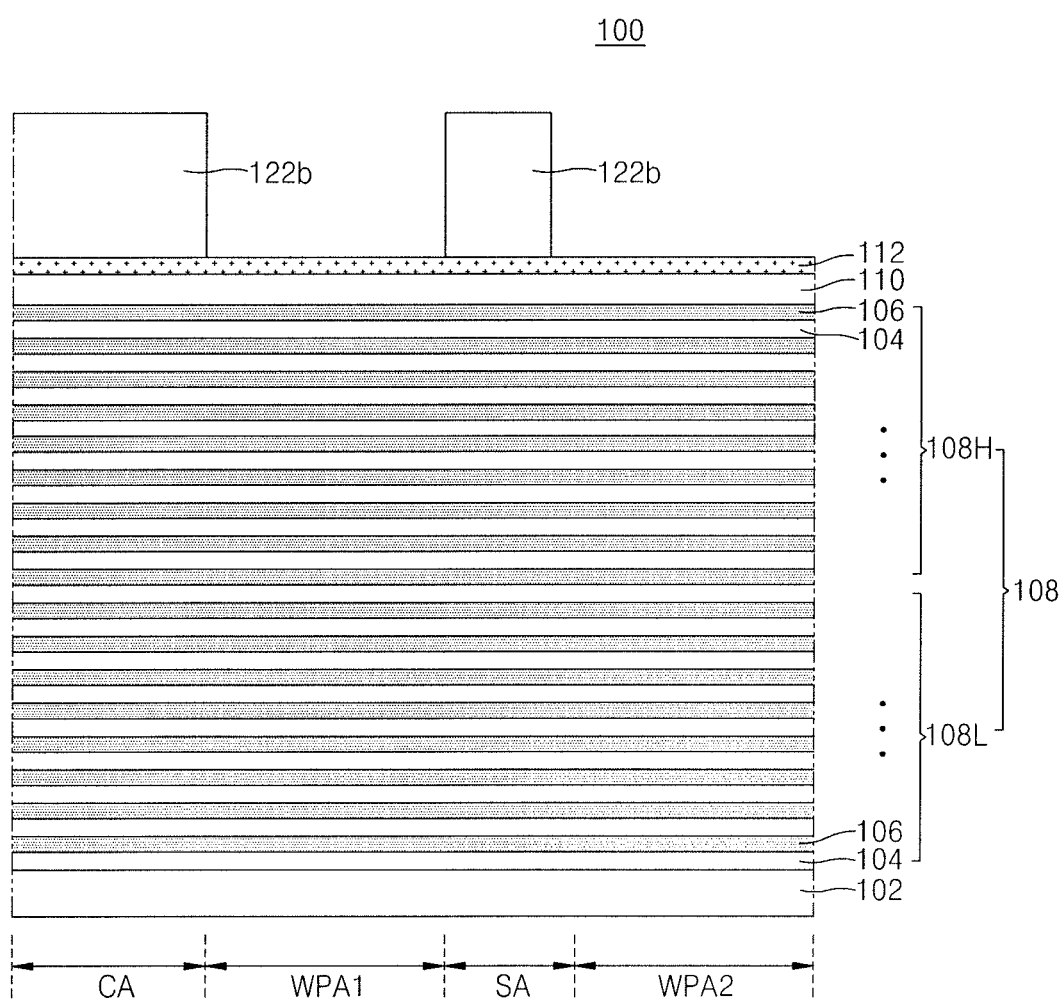
FIGS. 1A to 1H illustrate cross-sectional views showing stages in a method of fabricating a vertical semiconductor device according to a process order, according to an embodiment.

According to an embodiment, a photoacid generator (PAG) may be represented by the following Chemical Formula (I).

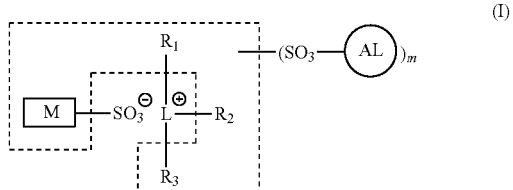

In Chemical Formula (I), L may be, e.g., sulfur (S) or iodine (I). For example, $R_3$ may be omitted when L is I. $R_1$, $R_2$, and $R_3$ may each independently be or include, e.g., a C1 to C10 linear, cyclic, or branched alkyl, alkenyl, alkynyl, or alkoxy group (which may be unsubstituted or substituted with a heteroatom such that the group may be bonded to L with an intervening heteroatom) or a C6 to C18 aryl, arylalkyl, or alkylaryl group (which may be unsubstituted or substituted with a heteroatom such that the group may be bonded to L with an intervening heteroatom). In an implementation, $R_1$, $R_2$, and $R_3$ may be separate or two of $R_1$, $R_2$, and $R_3$ may be bonded to each other and form a ring in conjunction with the sulfur or iodine atom in Chemical Formula (I). In an implementation, $R_1$, $R_2$, and $R_3$ may be monovalent groups or divalent linking groups. AL may be an acid-labile group. m may be, e.g., an integer of 1 to 4. M may be, e.g., a C1 to C30 linear, cyclic, or branched (e.g., monovalent or divalent) hydrocarbon group (which may be unsubstituted or substituted with a heteroatom such that the group may be bonded to S with an intervening heteroatom).

In an implementation, $R_1$, $R_2$, and $R_3$ may each independently be or include, e.g., an alkyl group such as a methyl, ethyl, n-propyl, isopropyl, n-butyl, tert-butyl, cyclopropyl, cyclopentyl, cyclohexyl, cyclopropylmethyl, 4-methylcyclohexyl, cyclohexylmethyl, norbornyl, or adamantyl group, an alkenyl group such as a vinyl, allyl, propenyl, butenyl, hexenyl, or cyclohexenyl group, an aryl group such as a phenyl, naphthyl, or thienyl group, an arylalkyl group such as a benzyl, 1-phenylethyl, or 2-phenylethyl group, or the like. In an implementation, some of hydrogen atoms in these groups may be substituted with heteroatoms such as oxygen, sulfur, nitrogen, or halogen atoms, or these groups may be intervened by a heteroatom such as oxygen, sulfur, or nitrogen atom. In an implementation, these groups may form or be interposed by hydroxyl groups, cyano groups, carbonyl groups, ether bonds, ester bonds, sulfonic acid ester bonds, carbonate bonds, lactone rings, sultone rings, carboxylic acid anhydrides, haloalkyl groups, or the like.

When L is iodine, $L^+(R_1R_2R_3)$ may be, e.g., a diphenyliodonium, bis(4-methylphenyl)iodonium, bis(4-ethylphenyl)iodonium, bis(4-tert-butylphenyl)iodonium, bis(4-(1,1-dimethylpropyl)phenyl)iodonium, 4-methoxyphenylphenyliodonium, 4-tert-butoxyphenylphenyliodonium, 4-acryloyloxyphenylphenyliodonium, or a 4-methacryloyloxyphenylphenyliodonium cation.

When L is sulfur, $L^+(R_1R_2R_3)$ may have, e.g., one of the following structures.

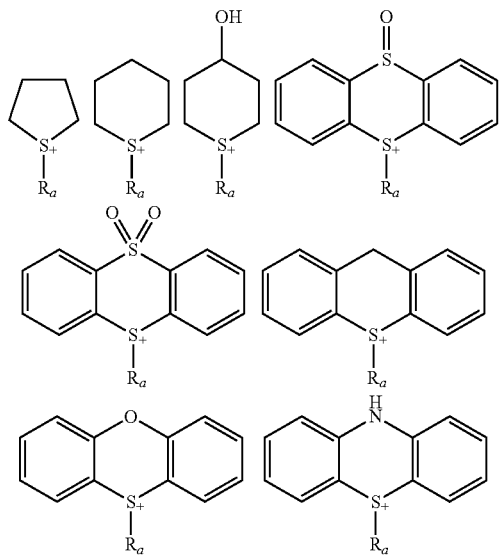

-continued

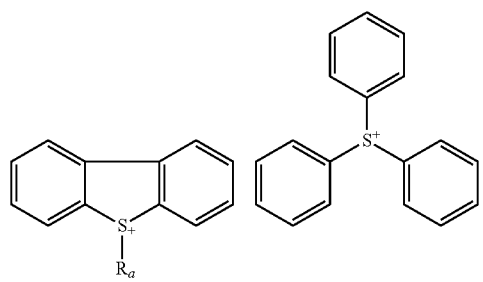

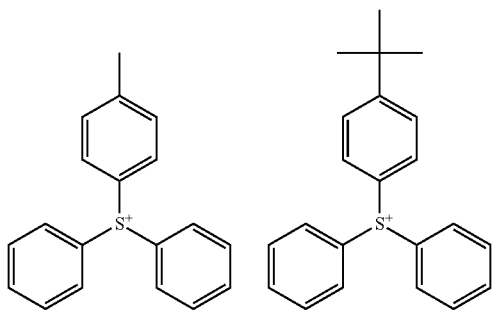

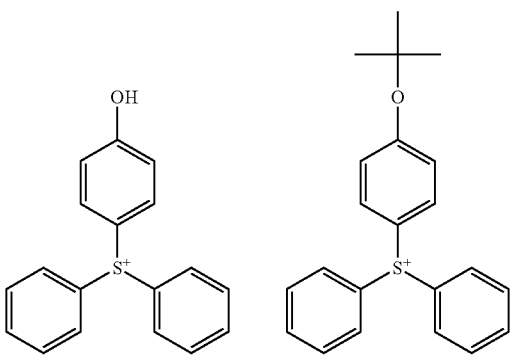

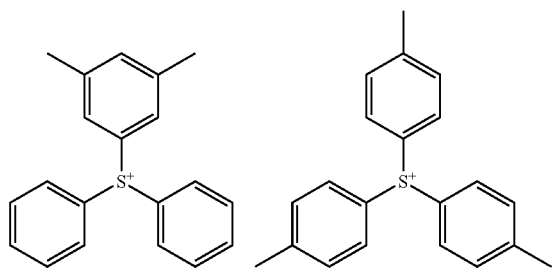

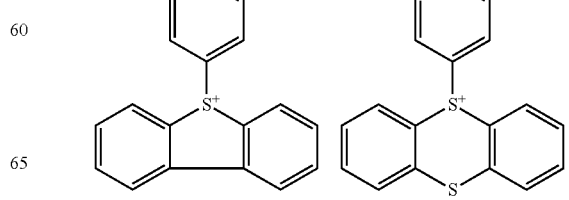

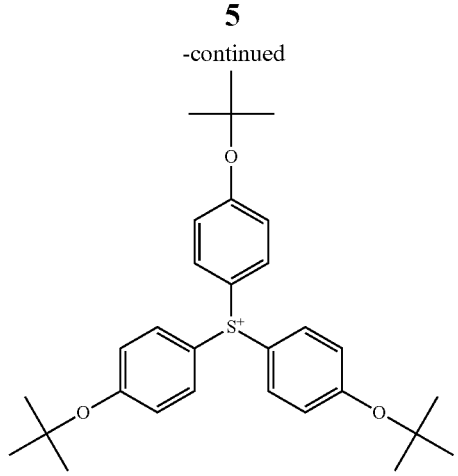
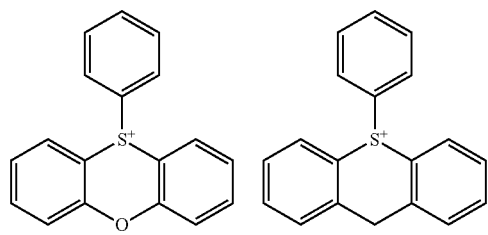
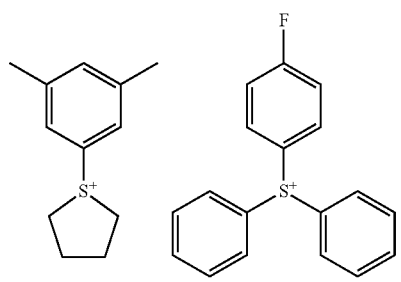
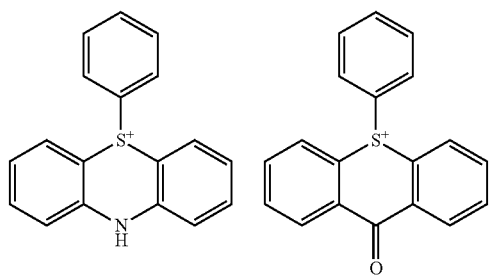
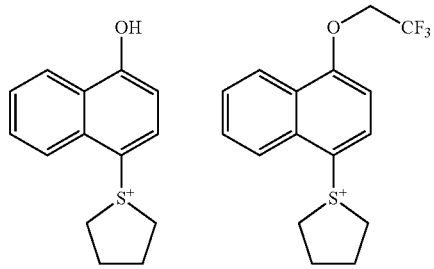

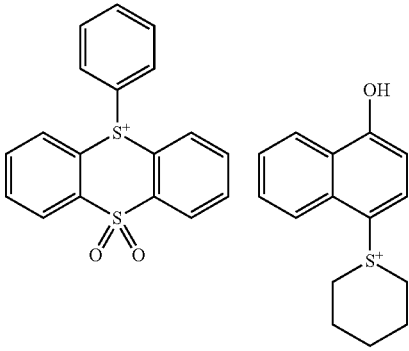
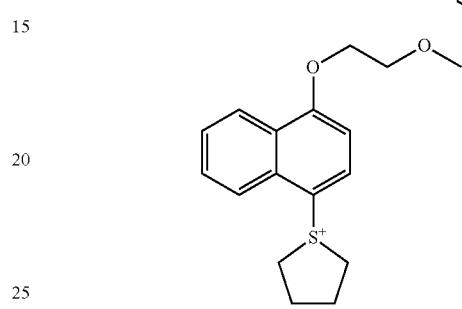
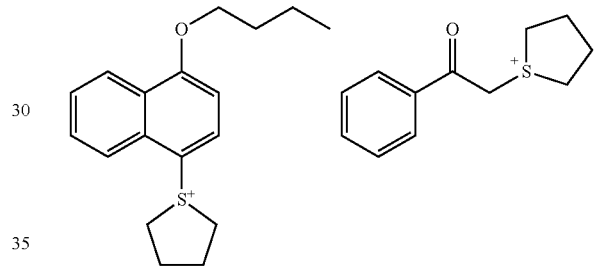

In the PAG represented by Chemical Formula (I), the functional group represented by —$SO_3$-AL may be bonded to the segment represented by M or to one of $R_1$, $R_2$, and $R_3$. In an implementation, the PAG may have two or more —$SO_3$-AL groups, at least one —$SO_3$-AL group may be bonded to the M segment, and at least one —$SO_3$-AL group may be bonded to one of $R_1$, $R_2$, and $R_3$. This will be described below in detail.

AL is a functional group that may be detached from the —$SO_3$ group. In an implementation, AL may include, e.g., a C4 to C15 tertiary alkyl group, —$Si(R_a R_b R_c)$, a C4 to C20 oxoalkyl group, or a group represented by one of the following Chemical Formulae (AL1) to (AL4).

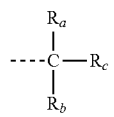
(AL1)

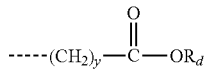
(AL2)

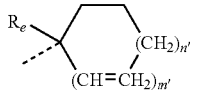
(AL3)

(AL4)

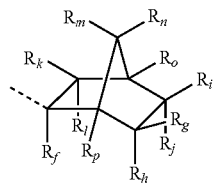

$R_a$ and $R_b$ may each independently be or include, e.g., a hydrogen atom or a C1 to C18 linear, cyclic, or branched alkyl group (which may be unsubstituted or substituted with a heteroatom such that the group may be bonded to Si or C with an intervening heteroatom). $R_c$ may be or may include, e.g., a C1 to C18 linear, cyclic, or branched alkyl group (which may be unsubstituted or substituted with a heteroatom such that the group may be bonded to Si or C with an intervening heteroatom). $R_d$ may be or may include, e.g., a C1 to C6 alkyl group-containing C4 to C20 trialkylsilyl group, a C4 to C20 oxoalkyl group, or a group represented by Chemical Formula (AL1). y may be, e.g., an integer of 0 to 6. $R_e$ and $R_f$ may each independently be or include, e.g., a C1 to C8 linear, cyclic, branched alkyl group or a C6 to C20 aryl group, or C7 to C20 alkylaryl or arylalkyl group (each of which may be unsubstituted or substituted with a heteroatom such that the group may be bonded to C with an intervening heteroatom and/or in which a hydrogen atom may be substituted or replaced with hydroxyl, alkoxy, carboxyl, alkoxycarbonyl, oxo, amino, alkylamino, cyano, mercapto, alkylthio, or sulfone groups. m' may be 0 or 1; n' may be an integer of 0 to 3; and 2m'+n' may be 2 or 3. $R_g$ to $R_p$ may each independently be or include, e.g., a hydrogen atom or a C1 to C15 monovalent linear, cyclic, or branched hydrocarbon group (in which a hydrogen atom may be substituted with hydroxyl, alkoxy, carboxyl, alkoxycarbonyl, oxo, amino, alkylamino, cyano, mercapto, alkylthio, or sulfone groups). In an implementation, $R_g$ to $R_p$ may be separate or two of $R_g$ to $R_p$ may be bonded to each other and form a ring.

In an implementation, AL may be, e.g., a functional group represented by one of the following Chemical Formulae (ALE001) to (ALE144). e.g., (ALE001) to (ALE090) and (ALE097) to (ALE144).

(ALE001)

(ALE002)

(ALE003)

(ALE004)

(ALE005)

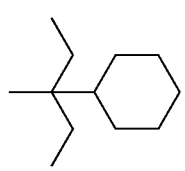

(ALE006)

(ALE007)

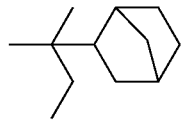

(ALE008)

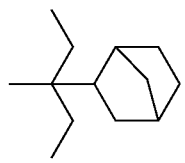

(ALE009)

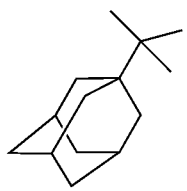

(ALE010)

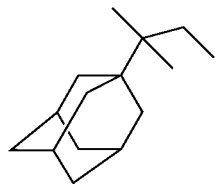

(ALE011)

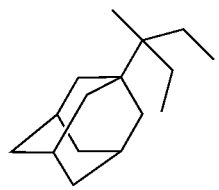

(ALE012)

(ALE013)

(ALE014)

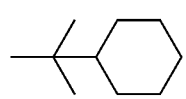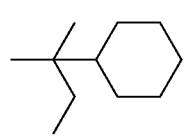

(ALE015)

(ALE016)
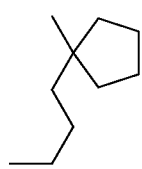
(ALE017)
(ALE018)
(ALE019)
(ALE020)
(ALE021)
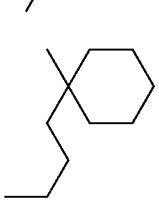
(ALE022)
(ALE023)
(ALE024)
(ALE025)
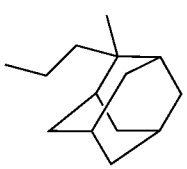
(ALE026)
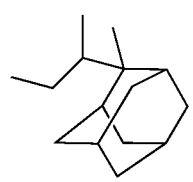
(ALE027)
(ALE028)
(ALE029)
(ALE030)
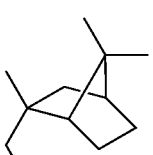
(ALE031)
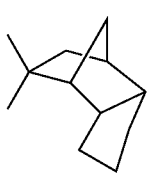
(ALE032)
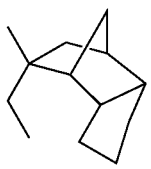
(ALE033)
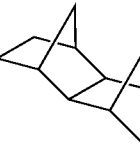
(ALE034)
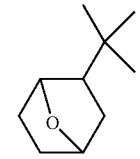

(ALE035)
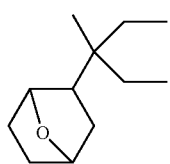
(ALE036)
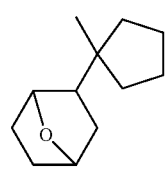
(ALE037)
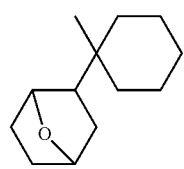
(ALE038)
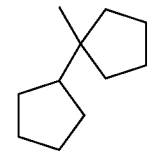
(ALE039)
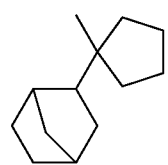
(ALE040)
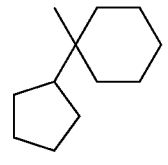
(ALE041)
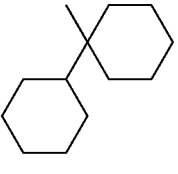
(ALE042)
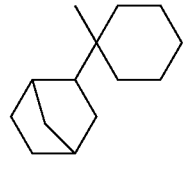
(ALE043)
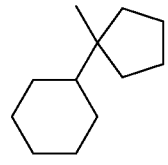
(ALE044)
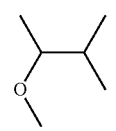
(ALE045)
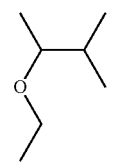
(ALE046)
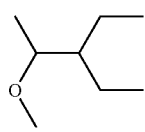
(ALE047)
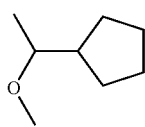
(ALE048)
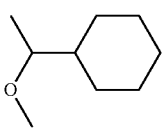
(ALE049)
(ALE050)
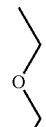
(ALE051)
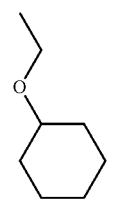
(ALE052)

(ALE053) 
(ALE054) 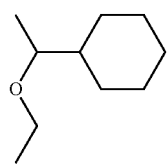
(ALE055) 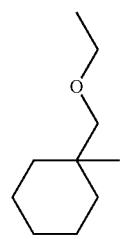
(ALE056) 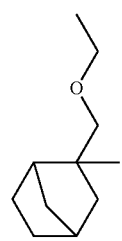
(ALE057) 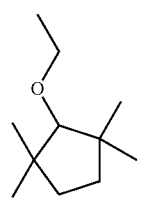
(ALE058) 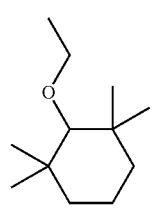
(ALE059) 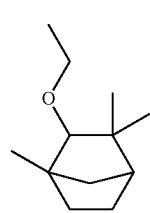
(ALE060) 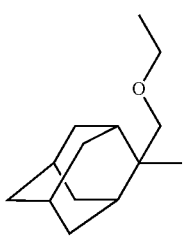
(ALE061) 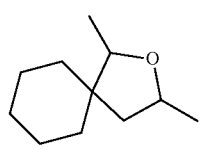
(ALE062) 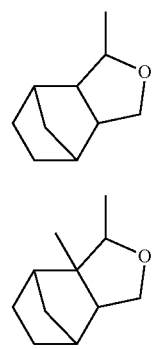
(ALE063) 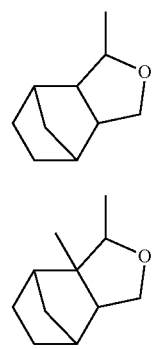
(ALE064) 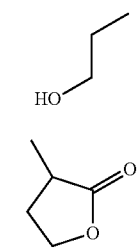
(ALE065) 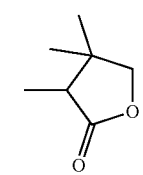
(ALE066) 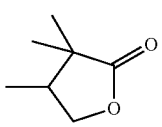
(ALE067) 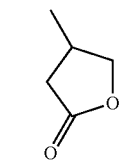
(ALE068) 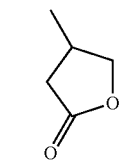
(ALE069) 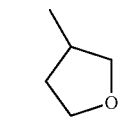

(ALE070)
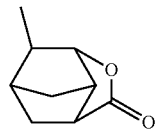
(ALE071)
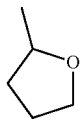
(ALE072)
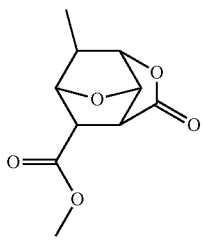
(ALE073)
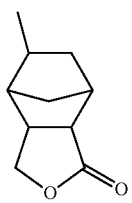
(ALE074)
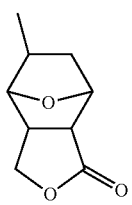
(ALE075)
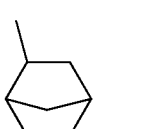
(ALE076)
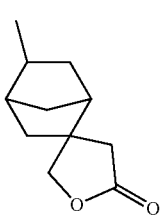
(ALE077)
(ALE078)
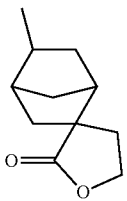
(ALE079)
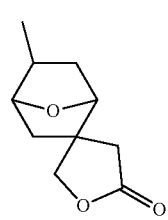
(ALE080)
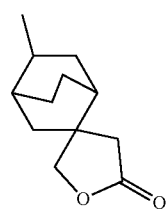
(ALE081)
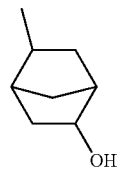
(ALE082)
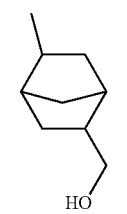
(ALE083)
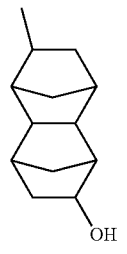
(ALE084)
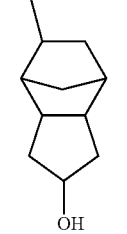

(ALE085)
(ALE086)
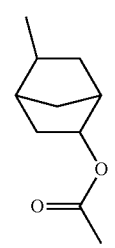
(ALE087)
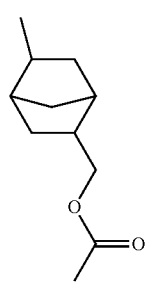
(ALE088)
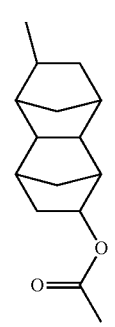
(ALE089)
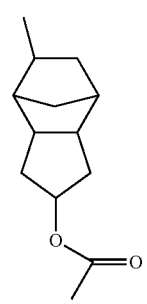
(ALE090)
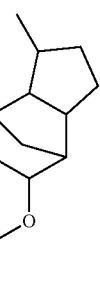
(ALE091)
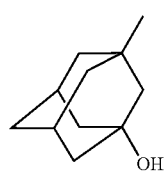
(ALE092)
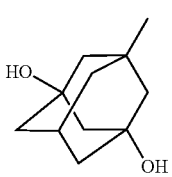
(ALE093)
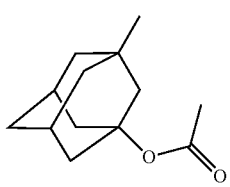
(ALE094)
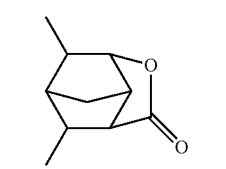
(ALE095)
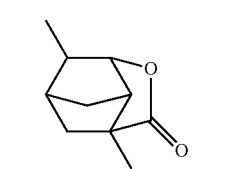
(ALE096)
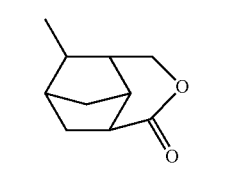
(ALE097)
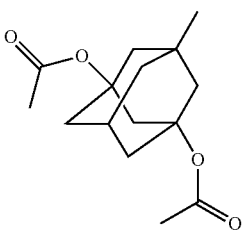

(ALE098)
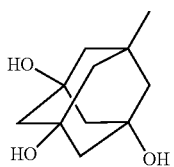
(ALE099)
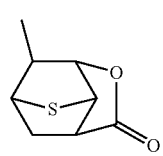
(ALE100)
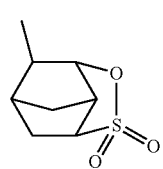
(ALE101)
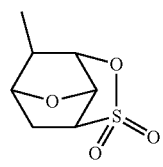
(ALE102)
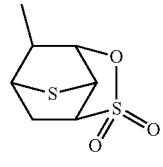
(ALE103)
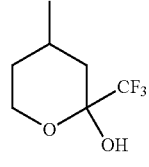
(ALE104)
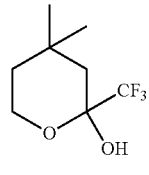
(ALE105)
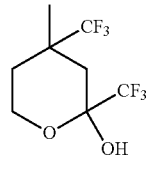
(ALE106)
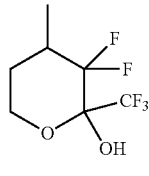
(ALE107)
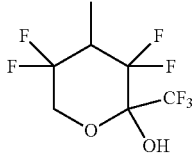
(ALE108)
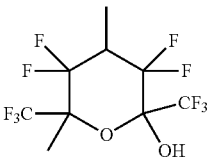
(ALE109)
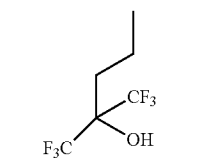
(ALE110)
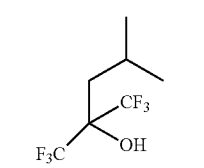
(ALE111)
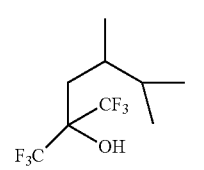
(ALE112)
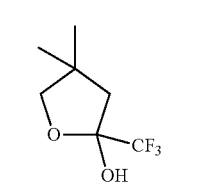
(ALE113)
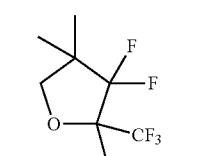
(ALE114)
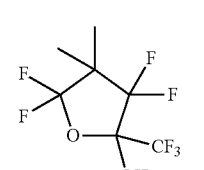
(ALE115)
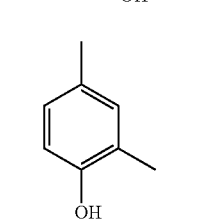

-continued
(ALE116)
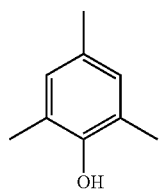
(ALE117)
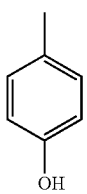
(ALE118)
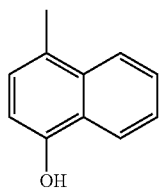
(ALE119)
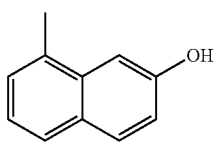
(ALE120)
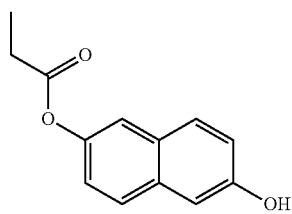
(ALE121)
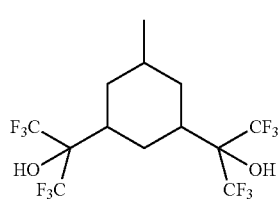
(ALE122)
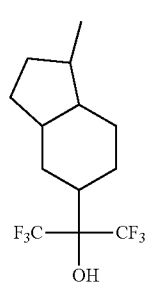
-continued
(ALE123)
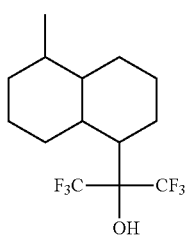
(ALE124)
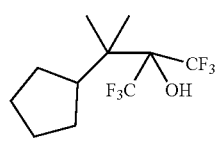
(ALE125)
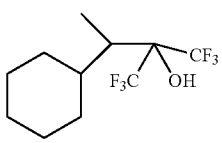
(ALE126)
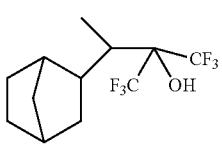
(ALE127)
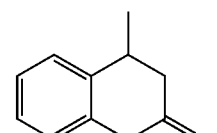
(ALE128)
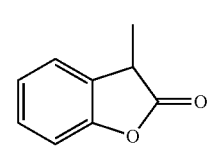
(ALE129)
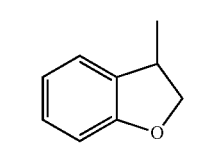
(ALE130)
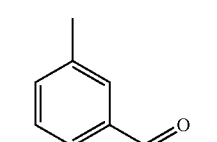
(ALE131)
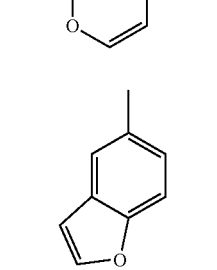

(ALE132)
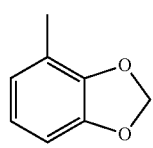
(ALE133)
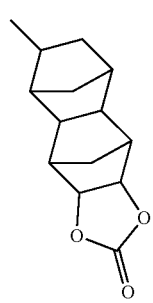
(ALE134)
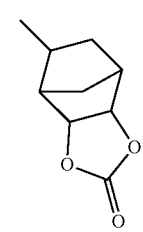
(ALE135)
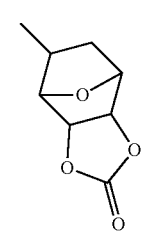
(ALE136)
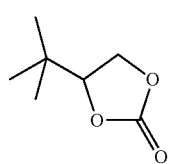
(ALE137)
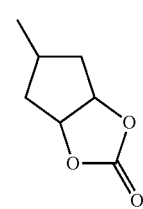
(ALE138)
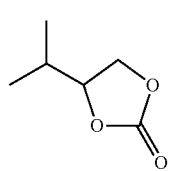
(ALE139)
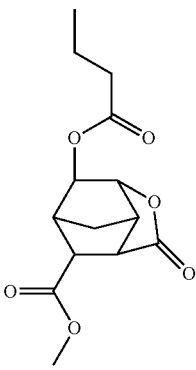
(ALE140)
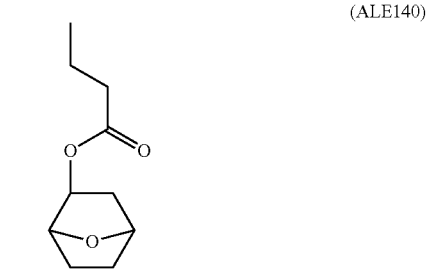
(ALE141)
(ALE142)
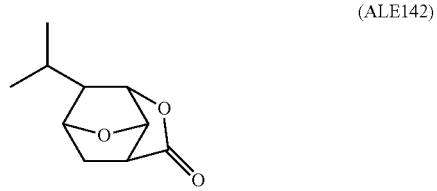
(ALE143)
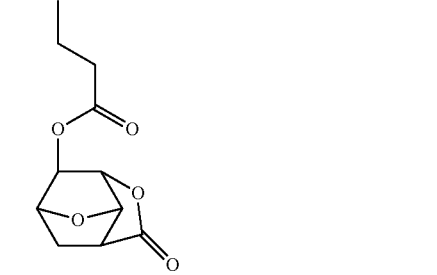
(ALE144)
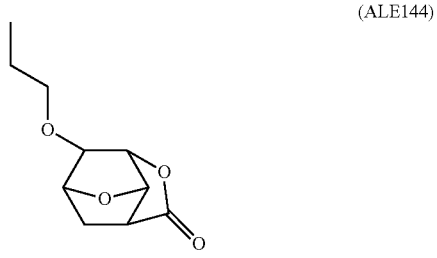

In an implementation, the PAG represented by Chemical Formula (I) may be a PAG represented by the following Chemical Formula (II). In the following Chemical Formulae, AL, M, $R_1$, $R_2$, and $R_3$ may be defined the same as those of Chemical Formula (I).

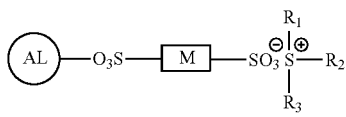

(II)

In an implementation, the PAG represented by Chemical Formula (I) may be a PAG represented by the following Chemical Formula (III).

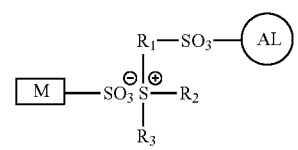

(III)

In an implementation, the PAG represented by Chemical Formula (I) may be a PAG represented by the following Chemical Formula (IV).

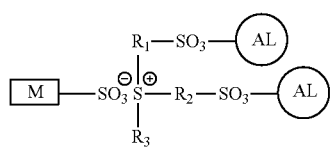

(IV)

In an implementation, the PAG represented by Chemical Formula (I) may be a PAG represented by the following Chemical Formula (V).

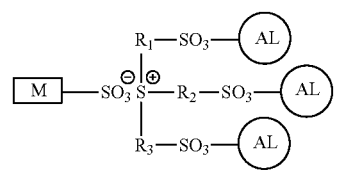

(V)

In an implementation, the PAG represented by Chemical Formula (I) may be a PAG represented by the following Chemical Formula (VI).

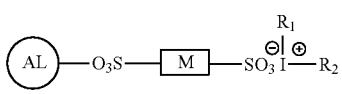

(VI)

In an implementation, the PAG represented by Chemical Formula (I) may be a PAG represented by the following Chemical Formula (VII).

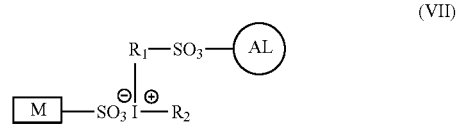

(VII)

In an implementation, the PAG represented by Chemical Formula (I) may be a PAG represented by the following Chemical Formula (VIII).

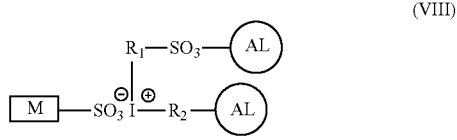

(VIII)

In an implementation, the PAG represented by Chemical Formula (I) may be a PAG represented by the following Chemical Formula (IX).

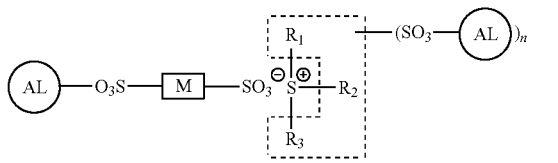

(IX)

In Chemical Formula (IX), n may be an integer of 1 to 3.

Although a sulfonium ion is shown in Chemical Formula (IX), it will be understood that an iodonium ion may be used instead of the sulfonium ion. In addition, when an iodonium ion is used, it will also be understood that $R_3$ may be omitted and n may be 1 or 2.

The PAG represented by Chemical Formula (I) may generate two acids with respect or in response to exposure to one photon. As used herein, the term "one photon" refers to a unit of light having minimum energy required for converting one $SO_3^-S^+(R_1R_2R_3)$ or $SO_3^-I^+(R_1R_2)$ into one acid, that is, one $SO_3^-H^+$ by dissociating the one $SO_3^-S^+(R_1R_2R_3)$ or $SO_3^-I^+(R_1R_2)$.

The principle by which two acids are generated by exposure to only one photon will be described hereinafter.

The following Reaction Formula 1 conceptually shows the principle of acid generation of a PAG having a structure represented by Chemical Formula (II).

<Reaction Formula 1>

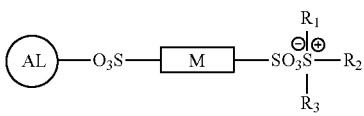

$\downarrow h\nu$

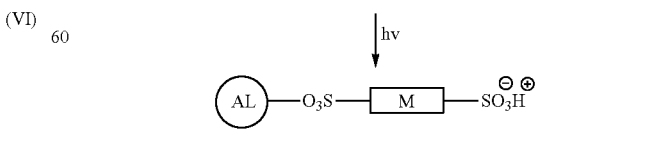

$\downarrow$

Referring to Reaction Formula 1, a sulfonium ion may be separated by incident light (hv), thereby generating an acid. Such acid generation may also be performed by other surrounding PAG's. The generated acid may act on an acid labile group (AL) attached to M and thus may generate another acid.

The following Reaction Formula 2 conceptually shows the principle of acid generation of a PAG having a structure represented by Chemical Formula (III).

<Reaction Formula 2>

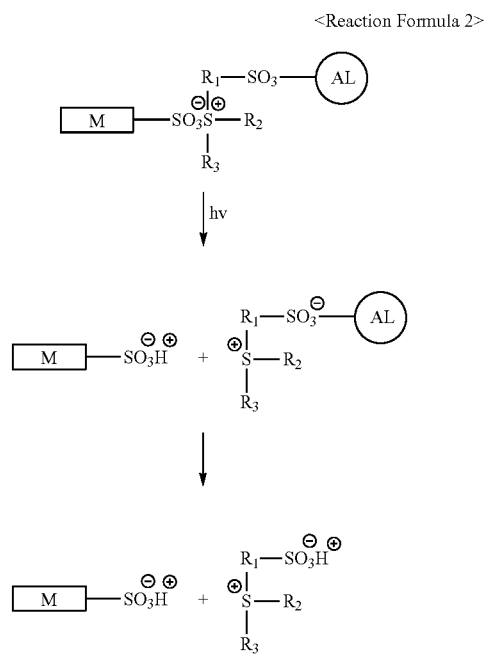

Referring to Reaction Formula 2, a sulfonium ion may be separated by incident light (by), thereby generating an acid. Such acid generation may also be performed by other surrounding PAG's. The generated acid may act on an acid labile group (AL) of the dissociated sulfonium ion and thus may generate another acid.

As described above, the PAG according to embodiments may generate two acids in response to exposure to only one photon, and the PAG according to embodiments may exhibit excellent photosensitivity even when used or included in a small amount. The PAG according to embodiments may not require an acid amplifier and thus may generate a large amount of acids without the loss of transmittance. In addition, the PAG according to embodiments may help reduce the need for heat treatment for acid diffusion and thus better pattern resolution may be realized.

As shown in the following chemical formula, when a PAG has a structure, in which two sulfate groups are present in one molecule and a sulfonium ion is attached to each of the two sulfate groups, the PAG in this case requires two photons and thus exhibits higher optical absorption than the PAG according to an embodiment.

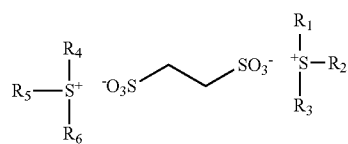

According to an embodiment, a photoresist material may include the PAG represented by Chemical Formula (I). The photoresist material may include, e.g., the PAG represented by Chemical Formula (I), a photosensitive resin, and a solvent capable of uniformly dissolving the PAG represented by Chemical Formula (I) and the photosensitive resin. In an implementation, the photoresist material may further include, e.g., a crosslinking agent, a quencher, a leveling agent, a surfactant, an antioxidant, an adhesion promoter, or the like, as desired. In an implementation, the PAG represented by Chemical Formula (I) may have a sufficient capability of acid generation, and an acid amplifier may not be required. In an implementation, the photoresist material may not include an acid amplifier.

The photosensitive resin may be a suitable photosensitive resin for photoresists, e.g., the photosensitive resin for photoresists exhibiting changed solubility with respect to a developer by reacting with an acid. In an implementation, the photosensitive resin may include a photosensitive polymer having an acid-sensitive protecting group that is detachable in response to an acid. In an implementation, the photosensitive polymer may be a block copolymer or a random copolymer.

The photosensitive resin may be, e.g., a positive photoresist. In an implementation, the positive photoresist may be, e.g., a photoresist for KrF excimer lasers (248 nm), a photoresist for ArF excimer lasers (193 nm), a photoresist for $F_2$ excimer lasers (157 nm), or a photoresist for extreme ultraviolet (EUV) (13.5 nm). The positive photoresist may include, e.g., a (meth)acrylate polymer. In an implementation, the (meth)acrylate polymer may be an aliphatic (meth) acrylate polymer, and may include, e.g., polymethylmethacrylate (PMMA), poly(t-butylmethacrylate), poly (methacrylic acid), poly(norbornylmethacrylate), binary or ternary copolymers of repeating units of the (meth)acrylate polymers set forth above, or mixtures thereof. In an implementation, the (meth)acrylate polymers may include various substituted acid-labile protecting groups. In an implementation, the protecting groups may include, e.g., tert-butoxycarbonyl (t-BOC) groups, tetrahydropyranyl groups, trimethylsilyl groups, phenoxyethyl groups, cyclohexenyl groups, tert-butoxycarbonyl methyl groups, tert-butyl groups, adamantyl groups, norbornyl groups, or the like.

In an implementation, the photosensitive resin may be a negative photoresist. In an implementation, the negative photoresist may be, e.g., a novolac resin or other suitable negative photoresist. For example, the negative photoresist may be obtained by reacting a phenol compound with an aldehyde or ketone compound in the presence of an acidic catalyst.

The phenol compound may include, e.g., phenol, ortho-cresol, meta-cresol, para-cresol, 2,3-dimethylphenol, 3,4-dimethylphenol, 3,5-dimethylphenol, 2,4-dimethylphenol, 2,6-dimethylphenol, 2,3,6-trimethylphenol, 2-t-butylphenol, 3-t-butylphenol, 4-t-butylphenol, 2-methylresorcinol, 4-methylresorcinol, 5-methylresorcinol, 4-t-butylcatechol, 2-methoxyphenol, 3-methoxyphenol, 2-propylphenol, 3-propylphenol, 4-propylphenol, 2-isopropylphenol, 2-methoxy-5-methylphenol, 2-t-butyl-5-methylphenol, thymol, isothymol, or the like. These phenol compounds may be used alone or in combination.

The aldehyde compound may include, e.g., formaldehyde, formalin, paraformaldehyde, trioxane, acetaldehyde, propylaldehyde, benzaldehyde, phenylacetaldehyde, α-phenylpropyl aldehyde, β-phenylpropylaldehyde, o-hydroxybenzaldehyde, m-hydroxybenzaldehyde, p-hydroxybenzaldehyde, o-chlorobenzaldehyde, m-chlorobenzaldehyde, p-chlorobenzaldehyde, o-methylbenzaldehyde, m-methylbenzaldehyde, p-methylbenzaldehyde, p-ethylbenzaldehyde, p-n-butylbenzaldehyde, terephthalic aldehyde, or the like. These aldehyde compounds may be used alone or in combination.

The ketone compound may include, e.g., acetone, methyl ethyl ketone, diethyl ketone, or diphenyl ketone. These ketone compounds may be used alone or in combination.

In an implementation, the photosensitive resin may have a weight average molecular weight of about 1,000 to about 500,000, as measured by gel permeation chromatography by using polystyrene as a standard. In an implementation, the photosensitive resin may be present in an amount of about 1% by weight (wt %) to about 60 wt %, based on a total weight of photoresist material.

Examples of the solvent may include butyl acetate, butyl propionate, ethyl lactate, methyl hydroxyacetate, ethyl hydroxyacetate, butyl hydroxyacetate, methyl methoxyacetate, ethyl methoxyacetate, butyl methoxyacetate, methyl ethoxyacetate, ethyl ethoxyacetate, methyl 3-oxypropionate, ethyl 3-hydroxypropionate, methyl 3-methoxypropionate, ethyl 3-methoxypropionate, methyl 3-ethoxypropionate, ethyl 3-ethoxypropionate, methyl 2-hydroxypropionate, propyl 2-hydroxypropionate, methyl 2-methoxypropionate, ethyl 2-methoxypropionate, propyl 2-methoxypropionate, methyl 2-ethoxypropionate, ethyl 2-ethoxypropionate, methyl 2-hydroxy-2-methylpropionate, ethyl 2-hydroxy-2-methylpropionate, methyl 2-methoxy-2-methylpropionate, ethyl 2-ethoxy-2-methylpropionate, methyl pyruvate, ethyl pyruvate, propyl pyruvate, methyl acetoacetate, ethyl acetoacetate, methyl 2-oxobutanoate, ethyl 2-oxobutanoate, dioxane, ethylene glycol, diethylene glycol, triethylene glycol, propylene glycol, dipropylene glycol, tripropylene glycol, 1,4-butanediol, ethylene glycol monoisopropyl ether, ethylene glycol monobutyl ether, propylene glycol monomethyl ether, propylene glycol monomethyl ether acetate, propylene glycol monoethyl ether acetate, propylene glycol monopropyl ether acetate, ethylene glycol monobutyl ether acetate, cyclohexanone, cyclopentanone, diethylene glycol monomethyl ether, diethylene glycol monomethyl ether acetate, diethylene glycol monoethyl ether, diethylene glycol monoethyl ether acetate, diethylene glycol monobutyl ether, diethylene glycol monobutyl ether acetate, diethylene glycol dimethyl ether, diethylene glycol diethyl ether, diethylene glycol methyl ethyl ether, toluene, xylene, γ-butyrolactone, N,N-dimethylacetamide, and mixtures thereof.

In an implementation, the solvent may be present in an amount of about 40 wt % to about 99 wt % based on the overall weight of the photoresist material.

In an implementation, the photoresist material may further include, e.g., a leveling agent and a surfactant, as desired. Examples of the leveling agent and the surfactant may include fluoroalkylbenzene sulfonates, fluoroalkyl carboxylates, fluoroalkyl polyoxyethylene ethers, fluoroalkyl ammonium iodides, fluoroalkyl betaines, fluoroalkyl sulfonates, diglycerin tetrakis(fluoroalkyl polyoxyethylene ethers), fluoroalkyl trimethylammonium salts, fluoroalkyl aminosulfonates, polyoxyethylene nonylphenyl ether, polyoxyethylene octylphenyl ether, polyoxyethylene alkyl ethers, polyoxyethylene lauryl ether, polyoxyethylene oleyl ether, polyoxyethylene tridecyl ether, polyoxyethylene cetyl ether, polyoxyethylene stearyl ether, polyoxyethylene laurate, polyoxyethylene oleate, polyoxyethylene stearate, polyoxyethylene lauryl amine, sorbitan laurate, sorbitan palmitate, sorbitan stearate, sorbitan oleate, sorbitan fatty acid esters, polyoxyethylene sorbitan laurate, polyoxyethylene sorbitan palmitate, polyoxyethylene sorbitan stearate, polyoxyethylene sorbitan oleate, polyoxyethylene naphthyl ether, alkylbenzene sulfonates, alkyl diphenyl ether disulfonates, and the like.

Each of the leveling agent and the surfactant may be present in an amount of about 0.001 wt % to about 0.1 wt %, based on the overall weight of the photoresist material.

In an implementation, the photoresist material may further include an adhesion promoter in order to improve adhesion to a substrate, as desired. The adhesion promoter may include, e.g., a silane, aluminum, or titanate compound. In an implementation, the adhesion promoter may include, e.g., 3-glycidoxypropyldimethylethoxysilane, 3-glycidoxypropylmethylethoxysilane, 3-glycidoxypropyltrimethoxysilane, acetoalkoxyaluminumdiisopropylate, tetraisopropylbis(dioctylphosphite)titanate, or the like.

The adhesion promoter may be present in an amount of about 0.1 wt % to about 10 wt %, based on the overall weight of the photoresist material.

In an implementation, the photoresist material may further include a quencher in order to adjust a diffusion rate of a material such as an generated acid or the like, as desired.

In an implementation, the quencher may include a primary, secondary, or tertiary amine compound, e.g., an amine compound which has a hydroxyl group, an ether bond, an ester bond, a lactone ring, a cyano group, or a sulfonic acid ester bond or is obtained by protecting a primary or secondary amine by using a carbamate group; an onium salt such as a sulfonium, iodonium, or ammonium salt of a carboxylic acid; or combinations thereof.

The quencher may be present in an amount of about 0.01 wt % to about 5 wt %, based on the overall weight of the photoresist material.

In an implementation, the photoresist material may further include a crosslinking agent, as desired.

In an implementation, the crosslinking agent may include a nitrogen-containing compound having at least two cross-link-forming substituents (e.g., methylol, methoxymethyl, or butoxymethyl groups). In an implementation, the crosslinking agent may include, e.g., hexamethoxymethylmelamine, tetramethoxymethylbenzoguanamine, 1,3,4,6-tetrakis(methoxymethyl)glycoluril, 1,3,4,6-tetrakis(butoxymethyl)glycoluril, 1,3,4,6-tetrakis(hydroxymethyl)glycoluril, 1,3-bis(hydroxymethyl)urea, 1,1,3,3-tetrakis(butoxymethyl)urea, 1,1,3,3-tetrakis(methoxymethyl)urea, or the like.

The crosslinking agent may be present in an amount of about 0.01 wt % to about 5 wt %, based on the overall weight of the photoresist material.

The photoresist material may exhibit reduced optical absorption and excellent photosensitivity even though only a small amount of the PAG according to embodiments is included. In addition, the photoresist material including the PAG according to embodiments may not require an acid amplifier and thus may have a low need for heat treatment for acid diffusion, and the photoresist material including the PAG according to embodiments may exhibit better pattern resolution.

Synthesis Example 1

1.7 g of 2-methylpropan-2-ol was added drop wise to a mixture of 6.3 g of (4-chlorosulfonylphenyl)diphenylsulfonium trifluoromethanesulfonate and 1.1 g of triethylamine (TEA) for reaction. The mixed reactants were stirred at room temperature for 1 hour, after which dilute hydrochloric acid was added to quench the reaction. The organic layer was taken out and washed with water. After adding diethyl ether, the supernatant was removed, obtaining 5.5 g of the product shown in Reaction Formula 3 (yield 81.2%).

<Reaction Formula 3>

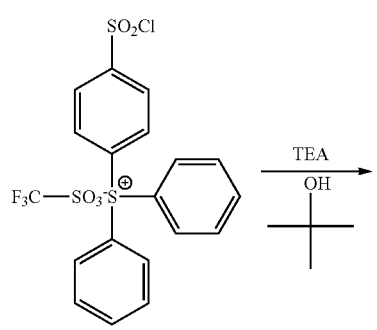

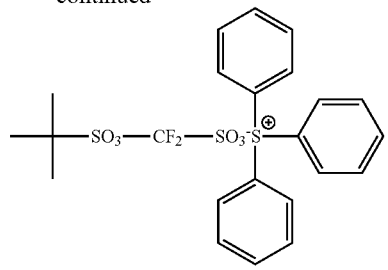

Synthesis Example 2

1.8 g of 2-methylpropan-2-ol was added drop wise to a mixture of 6.5 g of triphenylsulfonium chlorosulfonyl difluoromethanesulfonate and 1.0 g of triethylamine (TEA) for reaction. The mixed reactants were stirred at room temperature for 1 hour, after which dilute hydrochloric acid was added to quench the reaction. The organic layer was taken out and washed with water. After adding diethyl ether, the supernatant was removed, obtaining 5.1 g of the product shown in Reaction Formula 4 (yield 73.0%).

<Reaction Formula 4>

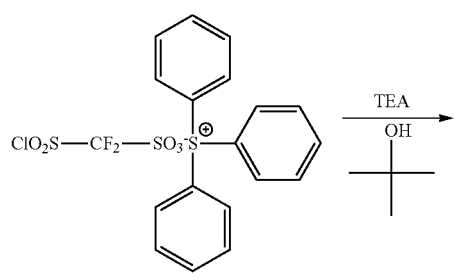

FIGS. 1A to 1H illustrate cross-sectional views showing stages in a method of fabricating a vertical semiconductor device 100 according to a process order, according to an embodiment.

Referring to FIG. 1A, a stacked structure 108 and a first capping layer 110 may be stacked, in this stated order, on a substrate 102 including a cell area CA, a sacrificial area SA, a first pad area WPA1, and a second pad area WPA2, and a polysilicon layer 112 is formed on the first capping layer 110. Next, first masks 122b may be formed on the polysilicon layer 112.

The stacked structure 108 may include an upper stacked structure 10811 and a lower stacked structure 108L. Each of the upper stacked structure 108H and the lower stacked structure 108L may include interlayer dielectrics 104 and sacrificial layers 106, which are repeatedly stacked. The interlayer dielectrics 104 may include insulating materials, e.g., silicon oxide. The sacrificial layers 106 may include materials having etch selectivity with respect to the interlayer dielectrics 104, e.g., silicon nitride layers, silicon oxynitride layers, polysilicon layers, or polysilicon germanium layers. In an implementation, the first capping layer 110 may include silicon oxide.

The polysilicon layer 112 may be formed by depositing an amorphous silicon layer, followed by applying heat to the amorphous silicon layer.

The first masks 122b may include photoresist layers formed by using a photoresist material including the PAG according to embodiments. An etch region of the stacked structure 108 may be defined by the first masks 122b. In addition, the PAG according to embodiments may exhibit excellent transparency and low optical absorption upon light exposure, as described above, and patterns having good resolution may be obtained despite the first masks 122b having high thicknesses.

Figure 1B:
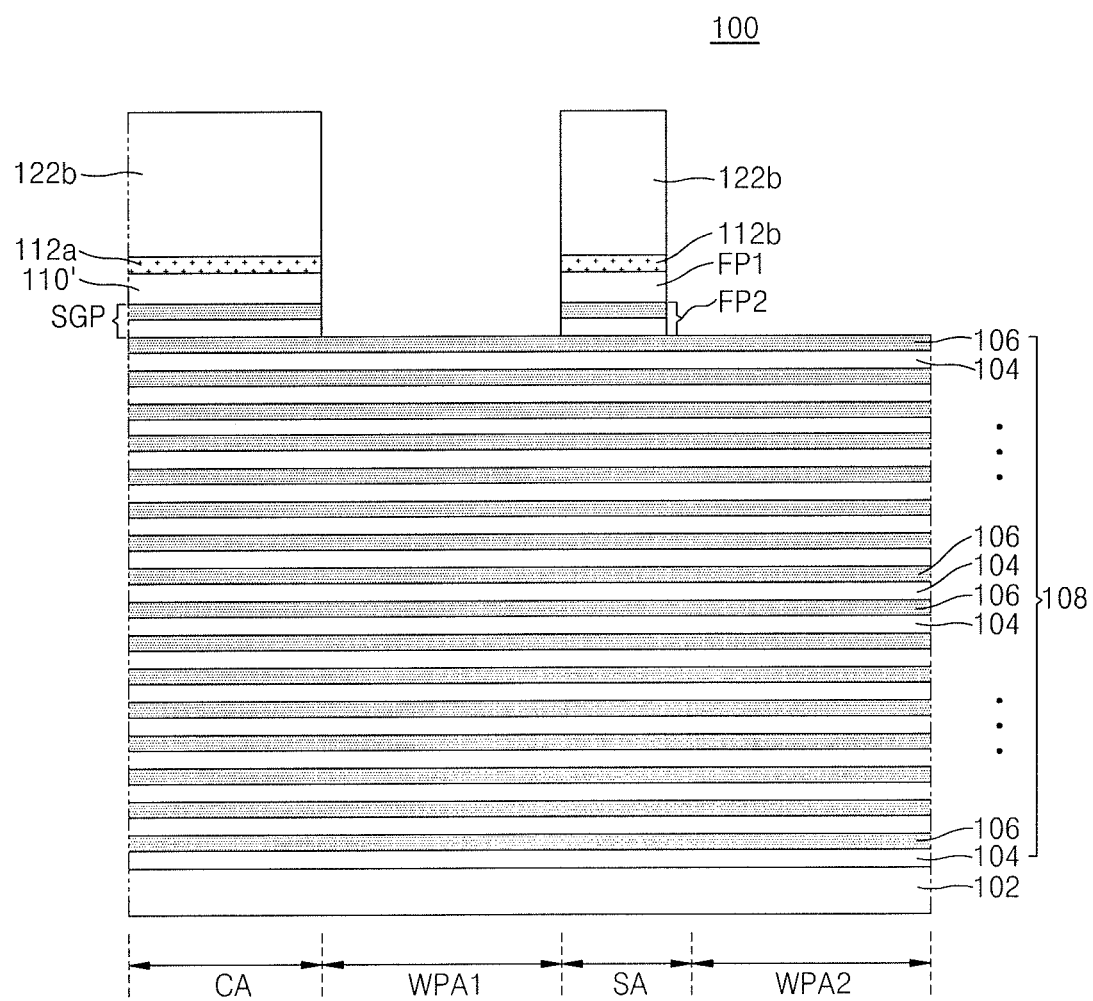

Referring to FIG. 1B, a first etching process may be performed to remove the polysilicon layer 112, the first capping layer 110 under the polysilicon layer 112, and a sacrificial layer 106 and an interlayer dielectric 104 under the first capping layer 110, in the first pad area WPA1 and the second pad area WPA1.

By the first etching process, a first polysilicon pattern 112a, a preliminary string selection gate pattern SGP, and a capping pattern 110' may be formed in the cell area CA, and a second polysilicon pattern 112b, a first floating pattern FP1 under the second polysilicon pattern 112b, and a second floating pattern FP2 under the first floating pattern FP1 may be formed in the sacrificial area SA.

The second polysilicon pattern 112b may act as an etch-preventive pattern for preventing an underlayer from being etched during a subsequent step-forming process, and the second polysilicon pattern 112b will be referred to as an etch-preventive pattern 112b, hereinafter.

Figure 1C:
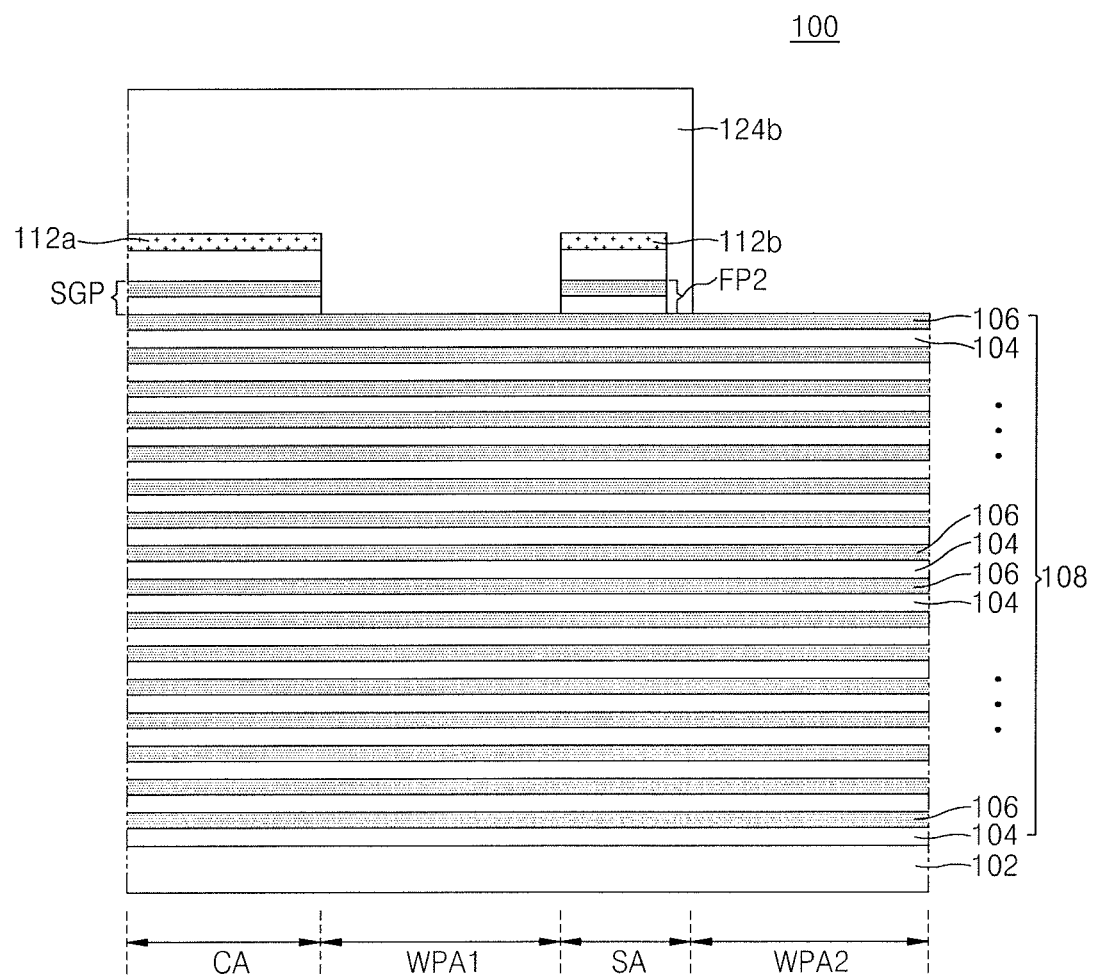

Referring to FIG. 1C, a second mask 124b may be formed on the cell area CA, the first pad area WPA1, and the sacrificial area SA. The second mask 124b may include a photoresist layer formed by using a photoresist material including the PAG according to embodiments.

Figure 1D:
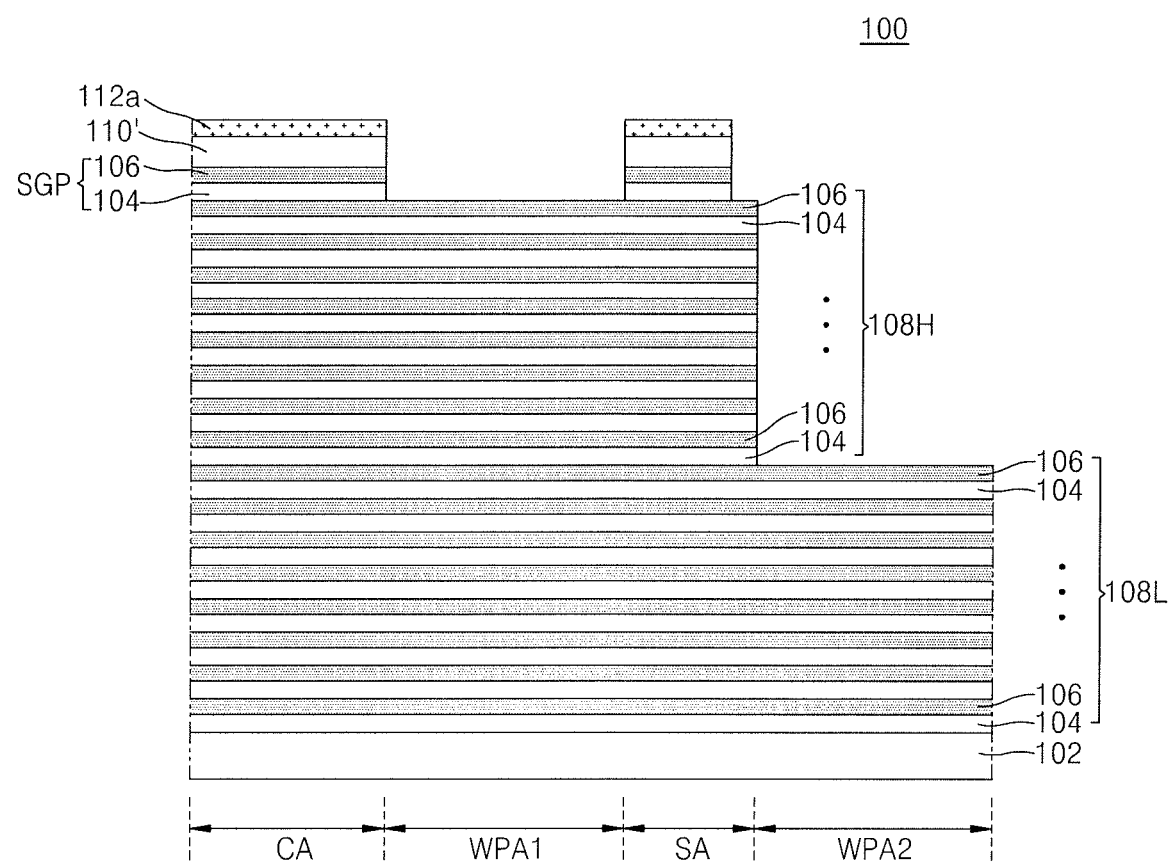

Referring to FIG. 1D, an upper preliminary stacked structure 108H corresponding to the second pad area WPA2 is removed, and the second mask 124b may be removed. Thus, only a lower preliminary stacked structure 108L may remain in the second pad area WPA2.

The second mask 124b may remain such that the cell area CA, the first pad area WPA1, and the sacrificial area SA are not exposed until the upper preliminary stacked structure 108H is completely removed, and the second mask 124b may have a sufficient thickness. If the photoresist layer constituting the second mask 124b were to absorb an excess of light upon light exposure, a high-resolution pattern may not be able to be obtained.

Figure 1E:
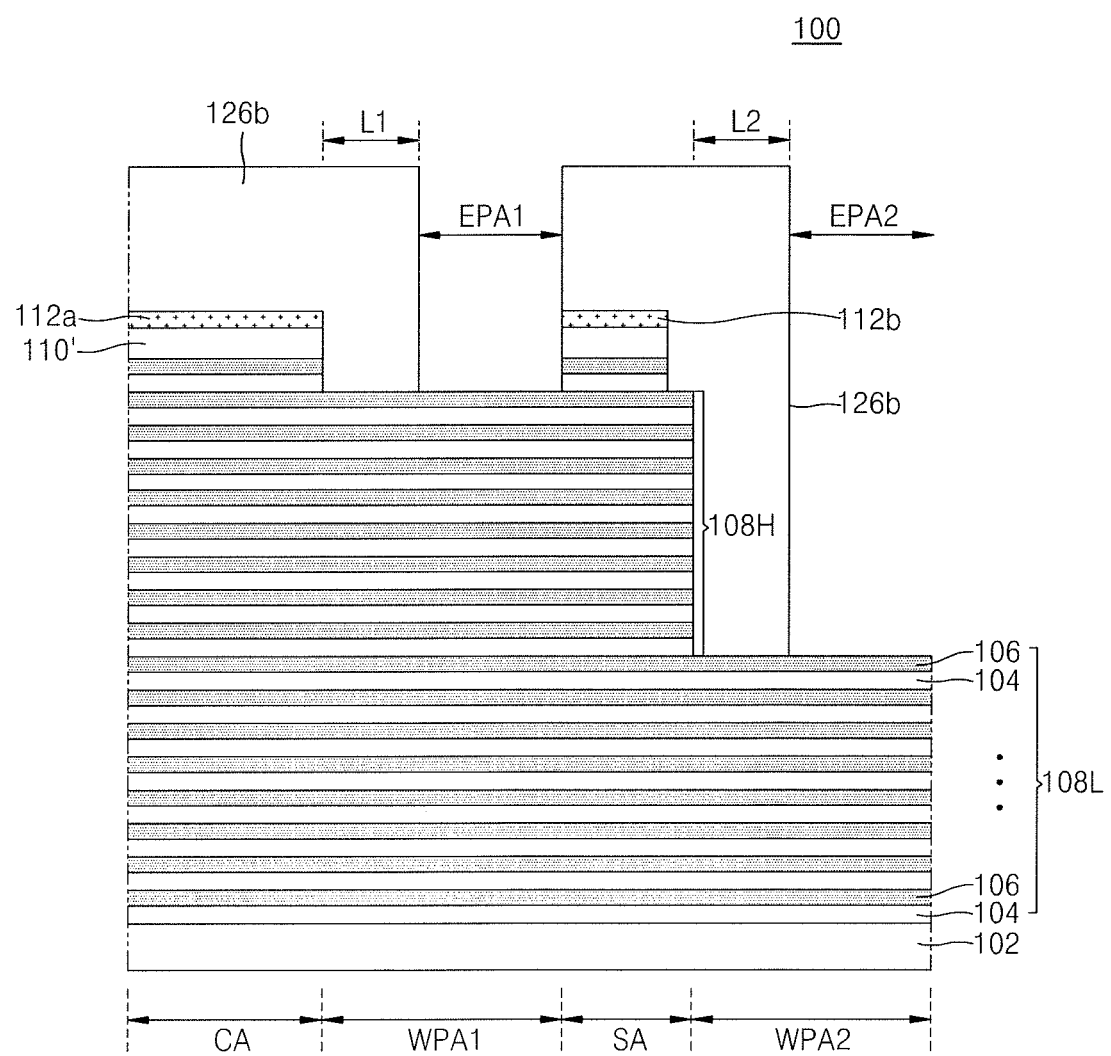

Referring to FIG. 1E, third masks 126b may be formed and may cover the overall cell area CA and a portion L1 of the first pad area WPA1 simultaneously with covering the overall sacrificial area SA and a portion L2 of the second pad area WPA2.

The third masks 126b may include photoresist layers formed by using a photoresist material including the PAG according to embodiments.

Blocking distances L1 and L2 of the first pad area WPA1 and the second pad area WPA2, which are respectively covered with the third masks 126b, may be equal to or greater than a value obtained by multiplying a horizontal length of one of exposed steps, which are to be subsequently formed, by the number of the steps.

A region of the first pad area WPA1, which is not covered with the third masks 126b, is referred to as a first exposed area EPA1, and a region of the second pad area WPA2, which is not covered with the third masks 126b, is referred to as a second exposed area EPA2.

Figure 1F:
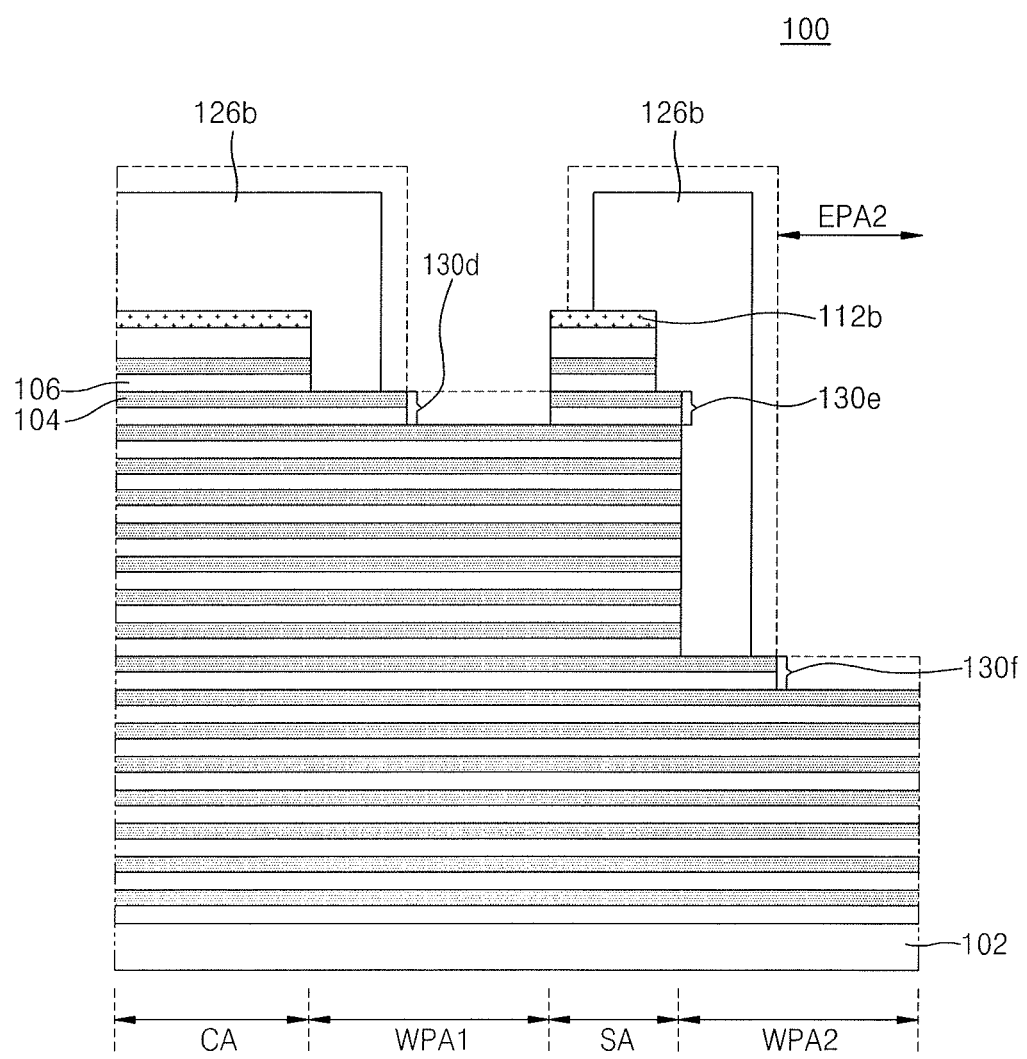

Referring to FIG. 1F, the method of fabricating the vertical semiconductor device 100 may include a first etching process for forming first patterns 130d and 130f respectively exposed in the first pad area WPA1 and the second pad area WPA2.

By the first etching process, sacrificial layers 106 respectively exposed in the first exposed area EPA1 and the second exposed area EPA2, and interlayer dielectrics 104 respectively underlying the sacrificial layers 106 may be removed while the third masks 126b are reduced from upper and side surfaces thereof. Therefore, while first patterns 130d, 130e, and 130f are respectively formed in the areas WPA1, SA, and WPA2, ends of the first patterns 130d and 130f may be respectively exposed in the first pad area WPA1 and the second pad area WPA2. The first pattern 130e separated from the first pattern 130d of the first pad area WPA1 may be formed in the sacrificial area SA, and one side surface of the separated first pattern 130e may be vertically aligned with one side surface of the etch-preventive pattern 112b above the first pattern 130e.

Figure 1G:
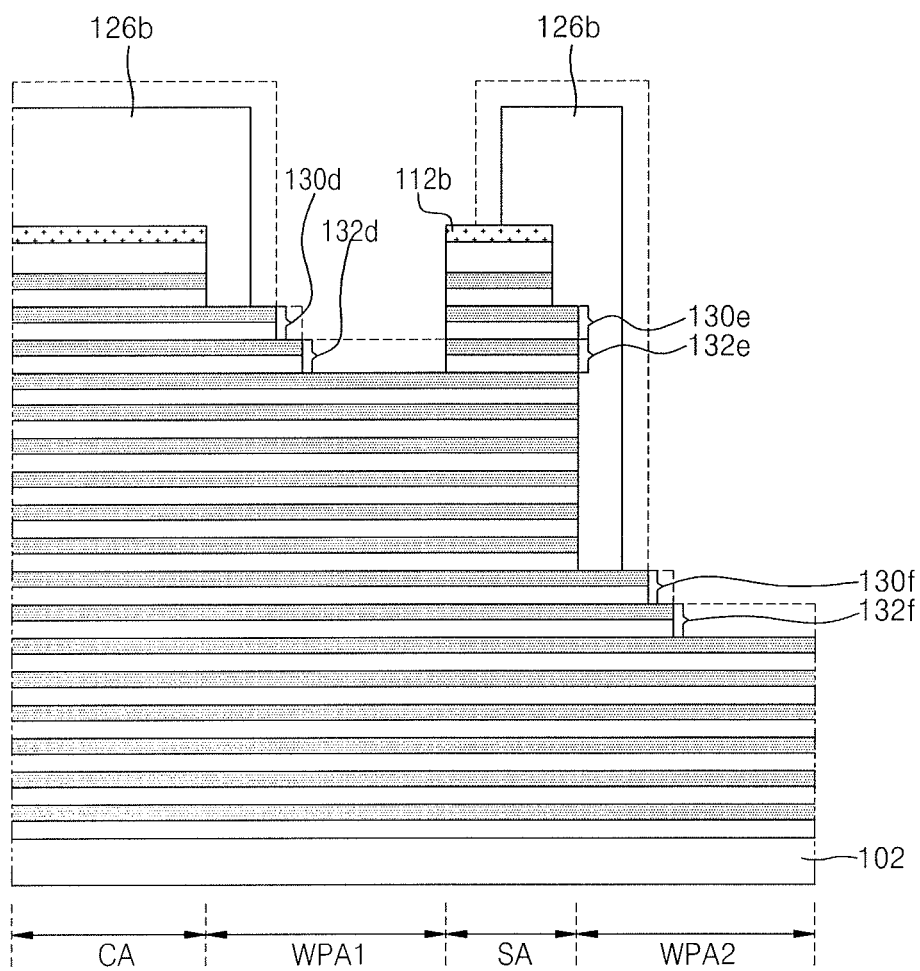

Referring to FIG. 1G, the method of fabricating the vertical semiconductor device 100 may include a second etching process for respectively forming second patterns 132d, 132e, and 132f under the first patterns 130d, 130e, and 130f, e.g., a step-forming process.

By the second etching process, while the second patterns 132d, 132e, and 132f are formed under the first patterns 130d, 130e, and 130f in the area WPA1, SA, and WPA2, respectively, step shapes may be formed by ends of the first patterns 130d and 130f and ends of the second patterns 132d and 132f, and the ends of the second patterns 132d and 132f may be exposed at sides of the third masks 126b.

The second pattern 132e separated from the second pattern 132d of the first pad area WPA1 may be formed in the sacrificial area SA, and one side surface of the second pattern 132e, which is adjacent to the first pad area WPA1, may be vertically aligned with one side surface of the first pattern 130e over the second pattern 132e.

Figure 1H:
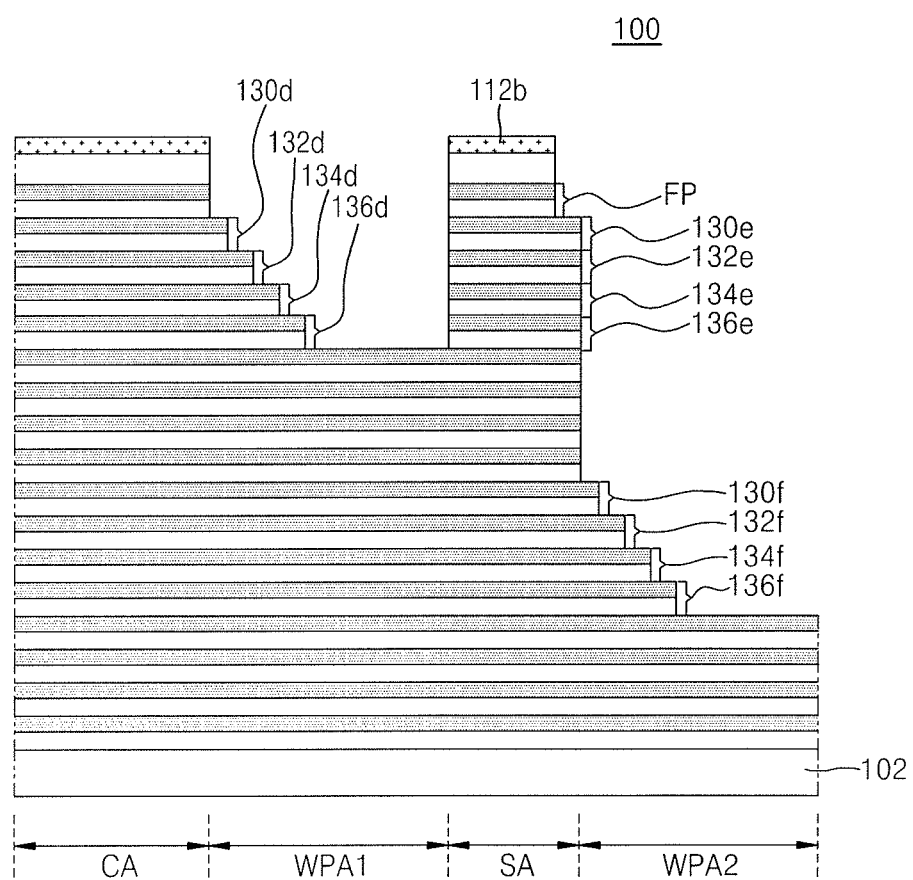

Referring to FIG. 1H, as a result of performing an etching process (step-forming process) multiple times by using the third masks 126b, as described above, the first patterns 130d and 130f, the second patterns 132d and 132f, third patterns 134d and 134f, and fourth patterns 136d and 136f may be simultaneously formed in the first pad area WPA1 and the second pad area WPA2. Side surfaces of first to fourth patterns 130e, 132e, 134e, and 136e in the sacrificial area SA may be vertically aligned, the side surfaces of the first to fourth patterns 130e, 132e, 134e, and 136e in the sacrificial area SA being adjacent to the first pad area WPA1. For example, the etch-preventive pattern 112b may be present in the sacrificial area SA (unlike in the first and second pad areas WPA1 and WPA2), and the first to fourth patterns 130e, 132e, 134e, and 136e under the etch-preventive pattern 112b may not be etched any more.

FIGS. 2A to 2D illustrate cross-sectional views showing stages in a method of fabricating an integrated circuit device 200 (see FIG. 2D) according to a process order, according to other embodiments.

Figure 2A:
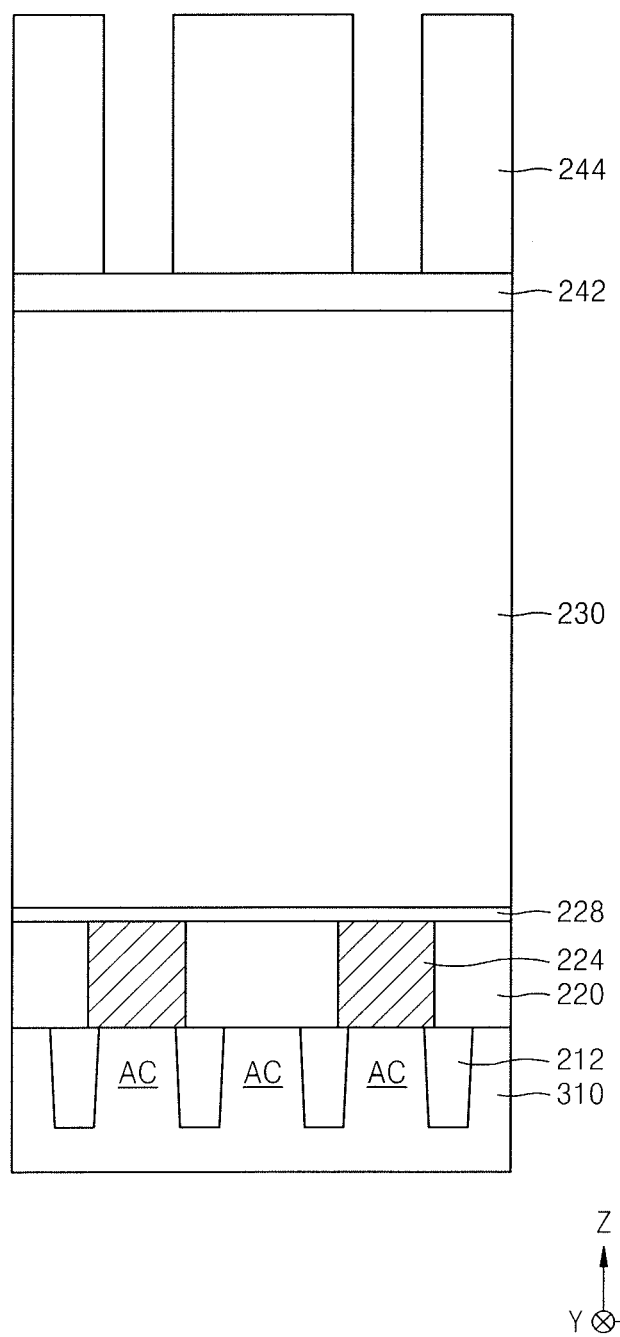
FIGS. 2A to 2D illustrate cross-sectional views showing stages in a method of fabricating an integrated circuit device according to a process order, according to other embodiments.

Referring to FIG. 2A, an interlayer dielectric 220 may be formed on a substrate 310 including a plurality of active regions AC, followed by forming a plurality of conductive regions 224, which may penetrate the interlayer dielectric 220 and may be respectively connected to the plurality of active regions AC.

The plurality of active regions AC may be defined by a plurality of device isolation regions 212. The device isolation regions 212 may include a silicon oxide layer, a silicon nitride layer, a silicon oxynitride layer, or combinations thereof. The interlayer dielectric 220 may include a silicon oxide layer.

The plurality of conductive regions 224 may include polysilicon, a metal, a conductive metal nitride, a metal silicide, or combinations thereof.

Next, an insulating layer 228 may be formed and may cover the interlayer dielectric 220 and the plurality of conductive regions 224. The insulating layer 228 may be used as an etch stop layer.

The insulating layer 228 may include an insulating material having etch selectivity with respect to the interlayer dielectric 220 and a mold layer 230 which is formed in a subsequent process. In an implementation, the insulating layer 228 may include silicon nitride, silicon oxynitride, or combinations thereof.

Next, the mold layer 230 may be formed on the insulating layer 228. The mold layer 230 may include an oxide layer. In an implementation, the mold layer 230 may include a support layer. The support layer may include a material having etch selectivity with respect to the mold layer 230.

Next, a sacrificial layer 242 and a mask pattern 244 may be formed on the mold layer 230 in this stated order.

The sacrificial layer 242 may include an oxide layer. The sacrificial layer 242 may protect the support layer included in the mold layer 230.

The mask pattern 244 may include a photoresist layer formed by using a photoresist material including the PAG according to embodiments. A region, in which a lower electrode of a capacitor is formed, may be defined by the mask pattern 244. In addition, as described above, the PAG according to embodiments may be heat-treated at a low temperature and thus may allow the deterioration in resolution of the photoresist layer due to diffusion to be reduced, and a more definite mask pattern 244 may be obtained.

Figure 2B:
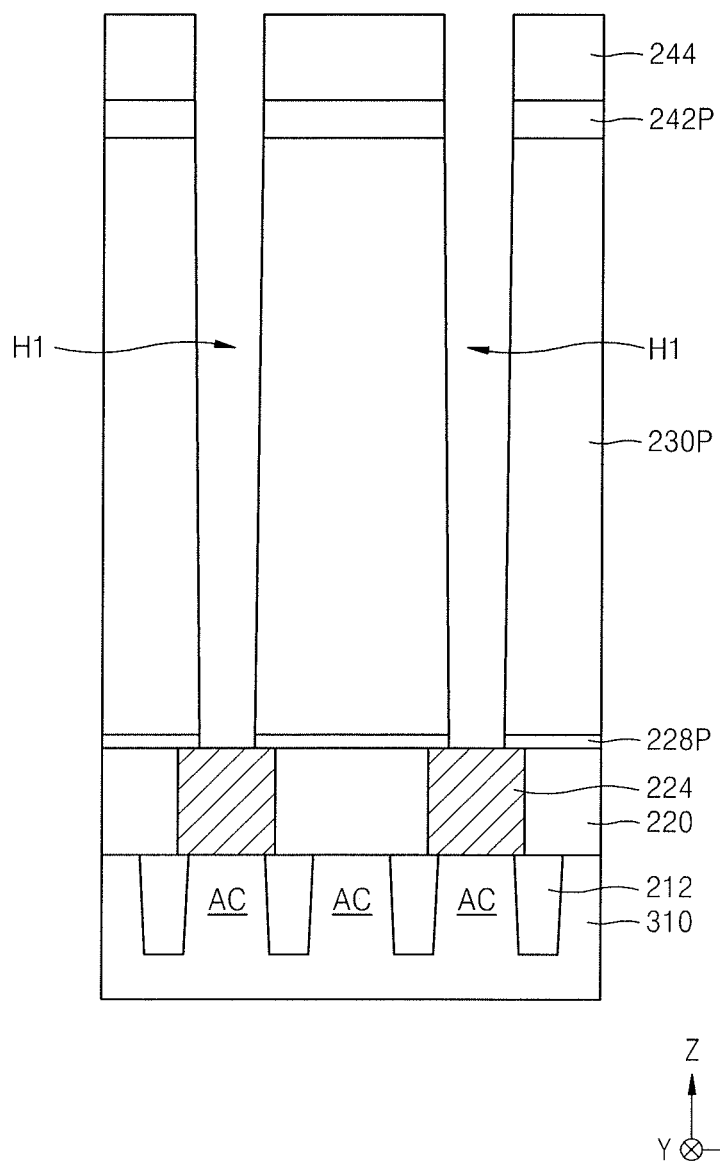

Referring to FIG. 2B, the sacrificial layer 242 and the mold layer 230 may be dry-etched by using the mask pattern 244 as an etch mask and using the insulating layer 228 as an etch stop layer, thereby forming a sacrificial pattern 242P and a mold pattern 230P, which define a plurality of holes H1. Here, the insulating layer 228 may also be etched due to overetch, whereby an insulating pattern 228P may be formed and expose the plurality of conductive regions 224.

Figure 2C:
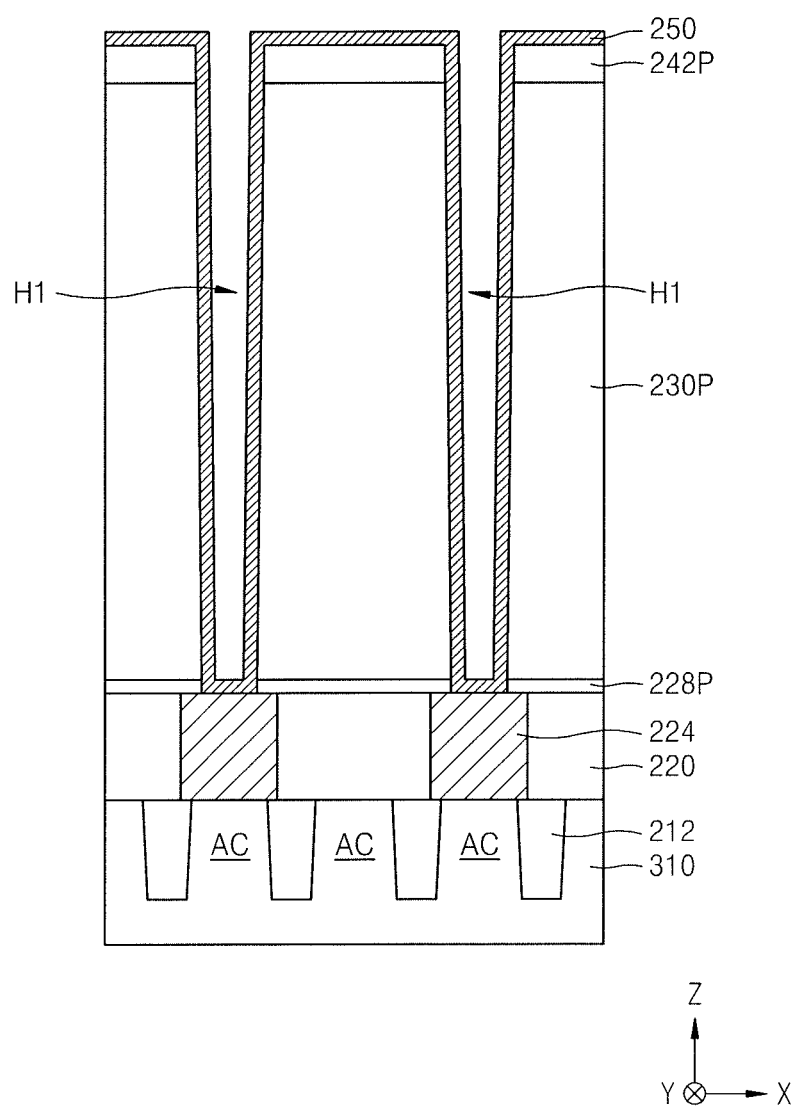

Referring to FIG. 2C, the mask pattern 244 may be removed from the resulting product of FIG. 2B, followed by forming a conductive layer 250 for forming lower electrodes, the conductive layer 250 for forming lower electrodes covering an inner sidewall of each of the plurality of holes H1, an exposed surface of the insulating pattern 228P, an exposed surface of each of the plurality of conductive regions 224 inside the plurality of holes H1, and an exposed surface of the sacrificial pattern 242P.

The conductive layer 250 for forming lower electrodes may be conformally formed on the sidewalls of the plurality of holes H1 such that an inner space of each of the plurality of holes H1 partially remains.

In an implementation, the conductive layer 250 for forming lower electrodes may include a doped semiconductor, a conductive metal nitride, a metal, a metal silicide, a conductive oxide, or combinations thereof. For example, the conductive layer 250 for forming lower electrodes may include TiN, TiAlN, TaN, TaAlN, W, WN, Ru, $RuO_2$, $SrRuO_3$, Ir, $IrO_2$, Pt, PtO, SRO ($SrRuO_3$), BSRO (($Ba,Sr$)$RuO_3$), CRO ($CaRuO_3$), LSCO (($La,Sr$)$CoO_3$), or combinations thereof. To form the conductive layer 250 for forming lower electrodes, a chemical vapor deposition (CVD), metal organic CVD (MOCVD), or atomic layer deposition (ALD) process may be used.

Figure 2D:
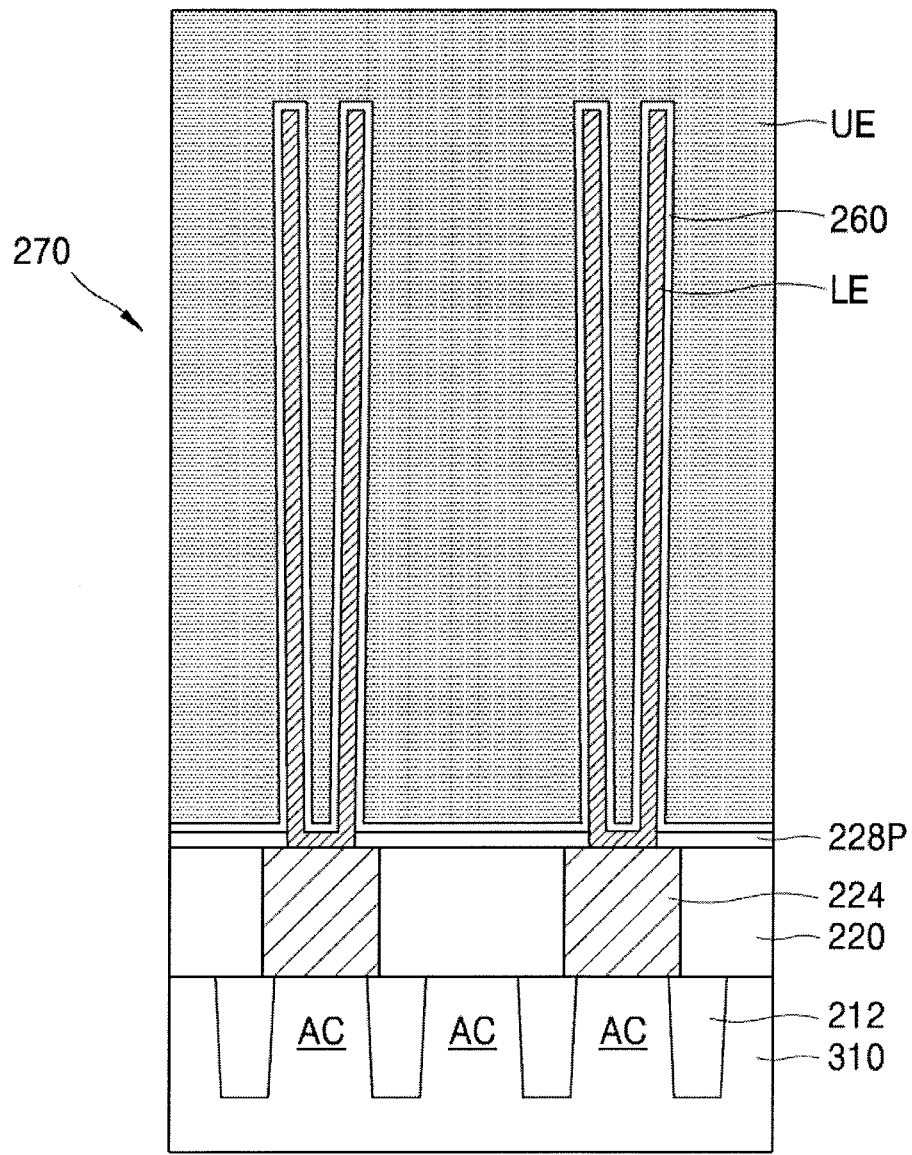

Referring to FIG. 2D, an upper portion of the conductive layer 250 for forming lower electrodes may be partially removed, thereby dividing the conductive layer 250 for forming lower electrodes into a plurality of lower electrodes LE.

To form the plurality of lower electrodes LE, an upper portion of the conductive layer 250 for forming lower electrodes and the sacrificial pattern 242P (see FIG. 2C) may be removed by an etch-back or chemical mechanical polishing (CMP) process such that an upper surface of the mold pattern 230P is exposed.

Next, the mold pattern 230P (see FIG. 2C) may be removed, thereby exposing outer sidewalls of the plurality of lower electrodes LE having cylindrical shapes. The mold pattern 230P may be removed by a lift-off process using LAL or hydrofluoric acid.

Next, a dielectric layer 260 is formed on the plurality of lower electrodes LE. The dielectric layer 260 may conformally cover exposed surfaces of the plurality of lower electrodes LE. The dielectric layer 260 may include a silicon oxide layer, a tantalum oxide layer, a zirconium oxide layer, an aluminum oxide layer, or combinations thereof. The dielectric layer 260 may be formed by an ALD process.

Next, an upper electrode UE may be formed on the dielectric layer 260. The lower electrodes LE, the dielectric layer 260, and the upper electrode UE may constitute a capacitor 270.

The upper electrode UE may include a doped semiconductor, a conductive metal nitride, a metal, a metal silicide, a conductive oxide, or combinations thereof. To form the upper electrode UE, a CVD, MOCVD, physical vapor deposition (PVD), or ALD process may be used.

By way of summation and review, if a photoacid generator is present in a large amount in a photoresist composition, the photoresist composition may exhibit increased optical absorption and thus deteriorated transmittance. A photoresist composition not exhibiting increased optical absorption and providing a high-resolution pattern may be desirable.

The embodiments may provide a photoacid generator that allows a photoresist composition to exhibit reduced optical absorption and excellent pattern resolution even though the photoacid generator is present in a small amount in the photoresist composition.

The embodiments may provide a photoresist composition exhibiting reduced optical absorption and excellent pattern resolution even though a photoacid generator is present in a small amount in the photoresist composition.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A photoacid generator (PAG) represented by the following Chemical Formula (I):

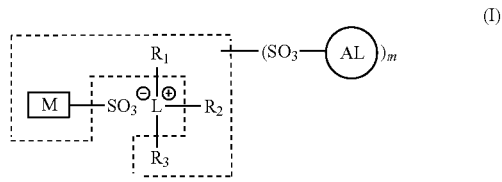

wherein, in Chemical Formula (I),

L is sulfur (S) or iodine (I), $R_3$ being omitted when L is I;

$R_1$, $R_2$, and $R_3$ are each independently:
a C1 to C10 linear, cyclic, or branched alkyl, alkenyl, alkynyl, or alkoxy group that is unsubstituted or substituted with a heteroatom such that the heteroatom is pendant or is between the group and L, or
a C6 to C18 aryl, arylalkyl, or alkylaryl group that is unsubstituted or substituted with a heteroatom such that the heteroatom is pendant or is between the group and L;

two of $R_1$, $R_2$, and $R_3$ being separate or being bonded to each other to form a ring in conjunction with L;

AL is an acid-labile group;

m is an integer of 1 to 4, at least one

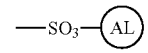

being bound to $R_1$, $R_2$, or $R_3$; and

M is a C1 to C30 linear, cyclic, or branched hydrocarbon group that is unsubstituted or substituted with a heteroatom such that the heteroatom is pendant or is between the group and a sulfur atom.

2. The PAG as claimed in claim 1, wherein the PAG represented by Chemical Formula (I) is represented by the following Chemical Formula (III), in which AL, M, R₁, R₂, and R₃ are defined the same as those of Chemical Formula (I),

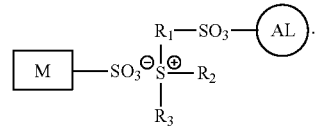

3. The PAG as claimed in claim 1, wherein the PAG represented by Chemical Formula (I) is represented by the following Chemical Formula (IV), in which AL, M, R₁, R₂, and R₃ are defined the same as those of Chemical Formula (I),

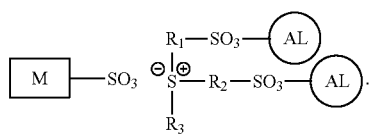

4. The PAG as claimed in claim 1, wherein the PAG represented by Chemical Formula (I) is represented by the following Chemical Formula (V), in which AL, M, R₁, R₂, and R₃ are defined the same as those of Chemical Formula (I),

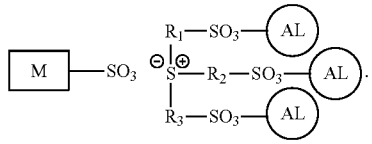

5. The PAG as claimed in claim 1, wherein the PAG represented by Chemical Formula (I) is represented by the following Chemical Formula (VII), in which AL, M, R₁, and R₂ are defined the same as those of Chemical Formula (I),

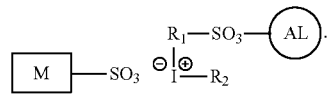

6. The PAG as claimed in claim 1, wherein the PAG represented by Chemical Formula (I) is represented by the following Chemical Formula (VIII), in which AL, M, R₁, and R₂ are defined the same as those of Chemical Formula (I),

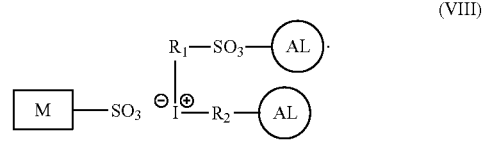

7. The PAG as claimed in claim 1, wherein the PAG represented by Chemical Formula (I) is represented by the following Chemical Formula (IX), in which AL, M, R₁, R₂, and R₃ are defined the same as those of Chemical Formula (I),

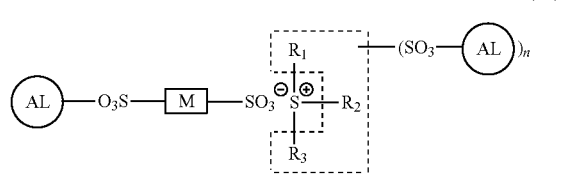

wherein n is an integer of 1 to 3.

8. The PAG as claimed in claim 1, wherein AL is detachable from the —SO₃ group by exposure to an acid.

9. The PAG as claimed in claim 8, wherein AL includes a C4 to C15 tertiary alkyl group, —Si($R_a R_b R_c$), a C4 to C20 oxoalkyl group, or a group represented by one of the following Chemical Formulae (AL1) to (AL4):

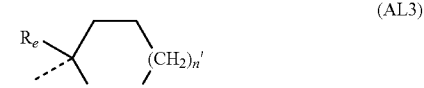

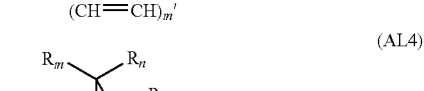

wherein, in the above groups, $R_a$ and $R_b$ are each independently a hydrogen atom or a C1 to C18 linear, cyclic, or branched alkyl group that is unsubstituted or substituted with a heteroatom such that the heteroatom is pendant or is between the group and Si or C;

$R_c$ is a C1 to C18 linear, cyclic, or branched alkyl group that is unsubstituted or substituted with a heteroatom such that the heteroatom is pendant or is between the group and Si or C;

$R_d$ is a C1 to C6 alkyl group-containing C4 to C20 trialkylsilyl group, a C4 to C20 oxoalkyl group, or a group represented by Chemical Formula (AL1);

y is an integer of 0 to 6;

$R_e$ and $R_f$ are each independently a C1 to C8 linear, cyclic, branched alkyl group, C6 to C20 aryl group or a C7 to C20 alkylaryl or arylalkyl group, each of $R_e$ and $R_f$ being unsubstituted or being substituted with a heteroatom, a hydroxyl group, an alkoxy group, a carboxyl group, an alkoxycarbonyl group, an oxo group, an amino group, an alkylamino group, a cyano group, a mercapto group, alkylthio group, or a sulfone group such that the heteroatom is pendant or is between the group and C;

m' is 0 or 1; n' is an integer of 0 to 3; and 2m'+n' is 2 or 3;

$R_g$ to $R_p$ are each independently a hydrogen atom, or a substituted or unsubstituted C1 to C15 monovalent linear, cyclic, or branched hydrocarbon group, in which a substituent of the substituted C1 to C15 monovalent linear, cyclic, or branched hydrocarbon group includes a hydroxyl group, an alkoxy group, a carboxyl group, an alkoxycarbonyl group, an oxo group, an amino group, an alkylamino group, a cyano group, a mercapto group, alkylthio group, or a sulfone group; and wherein two of $R_g$ to $R_p$ are separate or are bonded to each other and form a ring.

10. A photoresist composition, comprising:
a photosensitive resin;
a photoacid generator (PAG) represented by the following Chemical Formula (I); and
a solvent, the solvent being capable of dissolving the photosensitive resin and the photoacid generator represented by Chemical Formula (I),

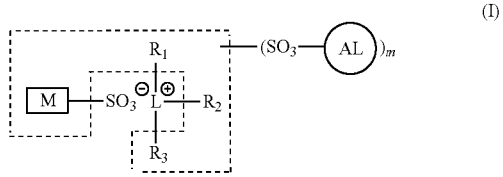

(I)

wherein, in Chemical Formula (I),
L is sulfur (S) or iodine (I), $R_3$ being omitted when L is I;

$R_1$, $R_2$, and $R_3$ are each independently:
  a C1 to C10 linear, cyclic, or branched alkyl, alkenyl, alkynyl, or alkoxy group that is unsubstituted or substituted with a heteroatom such that the heteroatom is pendant or is between the group and L, or
  a C6 to C18 aryl, arylalkyl, or alkylaryl group that is unsubstituted or substituted with a heteroatom such that the heteroatom is pendant or is between the group and L;
two of $R_1$, $R_2$, and $R_3$ being separate or being bonded to each other to form a ring in conjunction with L;
AL is an acid-labile group;
m is an integer of 1 to 4, at least one

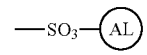

being bound to $R_1$, $R_2$, or $R_3$, and
M is a C1 to C30 linear, cyclic, or branched hydrocarbon group that is unsubstituted or substituted with a heteroatom such that the heteroatom is pendant or is between the group and a sulfur atom.

11. The photoresist composition as claimed in claim 10, wherein the composition does not include an acid amplifier.

12. The photoresist composition as claimed in claim 10, wherein the PAG represented by Chemical Formula (I) generates two acids in response to exposure to one photon.

13. A photoresist composition, comprising:
the PAG as claimed in claim 1;
a photosensitive resin; and
a solvent.

14. A method of manufacturing a device, the method comprising:
applying the photoresist composition as claimed in claim 13 on an object, and
exposing and developing the photoresist composition to form a pattern.

15. A method of manufacturing a device, the method comprising:
applying the photoresist composition as claimed in claim 10 on an object, and
exposing and developing the photoresist composition to form a pattern.

* * * * *